US008357643B2

(12) United States Patent
Benecke et al.

(10) Patent No.: US 8,357,643 B2
(45) Date of Patent: Jan. 22, 2013

(54) LUBRICANTS DERIVED FROM PLANT AND ANIMAL OILS AND FATS

(75) Inventors: Herman Benecke, Upper Arlington, OH (US); Bhima R. Vijayendran, Dublin, OH (US); Jeffrey Cafmeyer, Columbus, OH (US)

(73) Assignee: Battelle Memorial Institute, Columbus, OH (US)

( * ) Notice: Subject to any disclaimer, the term of this patent is extended or adjusted under 35 U.S.C. 154(b) by 933 days.

(21) Appl. No.: 11/573,494

(22) PCT Filed: Aug. 10, 2005

(86) PCT No.: PCT/US2005/028428

§ 371 (c)(1), (2), (4) Date: May 16, 2008

(87) PCT Pub. No.: WO2006/020716

PCT Pub. Date: Feb. 23, 2006

(65) Prior Publication Data

US 2010/0029523 A1 Feb. 4, 2010

(51) Int. Cl.
*C10M 105/36* (2006.01)
*C07C 59/00* (2006.01)
*C07C 51/00* (2006.01)

(52) U.S. Cl. ......... 508/496; 508/498; 554/148; 554/213

(58) Field of Classification Search .................. 508/496; 554/148, 213

See application file for complete search history.

(56) References Cited

U.S. PATENT DOCUMENTS

| | | | | |
|---|---|---|---|---|
| 5,075,046 | A | 12/1991 | Stoll | |
| 6,504,003 | B1 * | 1/2003 | Trout et al. | 528/271 |
| 6,583,302 | B1 * | 6/2003 | Erhan et al. | 554/213 |

FOREIGN PATENT DOCUMENTS

| | | |
|---|---|---|
| DE | 1 001 979 | 2/1957 |
| DE | 1941 522 | 3/1971 |
| JP | 58-134049 | 8/1983 |
| JP | 01-319458 | 12/1989 |
| JP | 08-259980 | 10/1996 |
| WO | WO 97/24313 | 7/1997 |

OTHER PUBLICATIONS

Office Action issued by the European Patent Office for corresponding EP Application No. 05 784 836.8, mailed Mar. 10, 2008-1221.

Response to Office Action issued by the European Patent Office for corresponding EP Application No. 05 784 836.8-1221, mailed Jul. 4, 2008.

* cited by examiner

*Primary Examiner* — Walter D Griffin
*Assistant Examiner* — Francis C Campanell
(74) *Attorney, Agent, or Firm* — Greer, Burns & Crain, Ltd.

(57) ABSTRACT

A lubricant from plant and/or animal oils and fats; methods for producing a lubricating oil, and the oil produced thereby. The lubricant is derived from an animal or plant fat or oil having an iodine number above about 7, and produced by epoxi-dising the fat or oil and (1) reacting the epoxidised fat or oil with a carboxylic acid anhydride in the presence of a basic catalyst to produce a diester, or (2) hydrogenating the epoxidised fat or oil to generate mono-alcohols and acylating the alcohol functionality with acid anhydrides, acid chlorides or carboxylic acids to produce a mono-ester.

36 Claims, 10 Drawing Sheets

Epoxidized Soybean Oil
(primarily linoleic acid arms)

Diacylated Soybean Oil
(Primarily linoleic acid arms)

PREPARATION OF SOYBEAN OIL DIESTERS

Epoxidized Soybean Oil
(primarily linoleic acid arms)

Diacylated Soybean Oil
(Primarily linoleic acid arms)

FIG. 1 PREPARATION OF SOYBEAN OIL DIESTERS

Epoxidized Soybean Oil
(Primarily Linoleic Acid):

Fully Hydrogenated ESO:

Acylated Hydrogenated ESO:

FIG. 2 PREPARATION OF SOYBEAN OIL MONOESTERS

LUBRICANTS DERIVED FROM PLANT AND ANIMAL OILS AND FATS

FIELD OF THE INVENTION

The present invention provides unique triglycerides useful in industrial fluids that are derived from renewable feedstocks such as plant and animal oils and fats. The industrial fluids are useful as engine oils (typically two cycle, four cycle, Wankel, and turbine type engines), hydraulic fluids, drive oils, metal working fluids, greases, general lubricants, brake fluids rock drilling fluid and the like. The present invention also provides materials that may be used as additives for lubricants to enhance or modify their properties (e.g. viscosity enhancement).

BACKGROUND OF THE INVENTION

Major problems in using oils from renewable feedstocks such as plant oils, (i.e. soybean oils and other vegetable oils), or oils or fats derived from animal sources, (e.g. menhaden, lard, butterfat and other animal derived oils) as various type lubricants are: (1) their low oxidative stability; (2) their relatively low viscosities; and (3) tendencies to solidify at low operating temperatures as manifested by relatively high pour points (temperatures below which they will no longer pour). However, successful modification of animal or vegetable oils or fats that overcomes these liabilities should reduce the U.S. dependence on foreign oil, since these lubricant candidates would be derived from renewable feedstocks. Lubricants derived from renewable feedstocks are also typically biodegradable. A typical renewable feedstock oil is represented by soybean oil. In fact, soybean oil is a preferred oil due to its high availability and relatively low cost.

An important driver towards the use of biodegradable lubricants is the worldwide misuse of mineral based lubricants. Of the approximately 1200 million gallons of lubricants used in Europe in 1990, about 170 million gallons (13%) disappeared into the environment. In the United States, of the approximately 1350 million gallons used about 430 million gallons (32%) ended up in landfills or were dumped. Recent studies from 2002, estimate that about 50% of lubricants worldwide end up in the environment.

Erhan, et al (U.S. Pat. No. 6,583,302 hereafter referred to as Erhan) discloses that vicinal diesters of plant oil triglycerides can be produced by reacting epoxidized triglycerides (e.g. epoxidized soybean oil) by a two-step and a one-step procedure. In the two-step procedure, epoxidized soybean oil is reacted with water in the presence of the Bronsted acid perchloric acid to produce putative vicinal diols along the fatty acid chains. This mixture is then reacted with various acid anhydrides to produce putative vicinal diester structures along the fatty acid chains.

Based on literature precedents, the amount of vicinal diester products of the type shown above obtained by either of the two processes is believed to be about 25%. The majority (about 75%) of the product is expected to consist of tetrahydrofuranyl (oxolane) substructures bearing two ester groups.

It is well known and described in the open literature that methylene-interrupted bis-epoxides will generate tetrahydrofuranyl diols in nearly quantitative yields when reacted with water in the presence of either Bronsted or Lewis acids.

Thus, in a two step process (which uses a Bronsted acid), the tetrahydrofuranyl diols would be produced from linoleate and linolenate fatty acids (each of which have methylene-interrupted bis-epoxide structures) and these diols would then be acylated to form tetrahydrofuranyl diesters.

Erhan's one step process uses the Lewis acid catalyst boron trifluoride and this one step process uses acid anhydride without the involvement of water. It is presently believed that the same tetrahydrofuranyl structures that are formed in two-step process are also formed in the one-step approach since Erhan's patent implies that products obtained by both processes have similar NMR spectra. Also, both the microoxidation and pressurized differential scanning calorimetry data from the two-step and the one-step process are very similar. Also, the microoxidation results reported by Erhan show very significant percent volatile loss and percent insoluble deposit that is very much higher than those reported in the present invention where vicinal diesters are actually produced. These high oxidative decomposition pathways are consistent with tetrahydrofuranyl ring structures that are known to be very susceptible to oxidative decomposition.

In epoxidized soybean oil, approximately 75% of all epoxide groups are of the methylene bis-epoxide type and will thus produce the tetrahydrofuranyl diester system under both reaction approaches described by Erhan.

In contrast to Erhan, the present invention uses basic catalysts to convert epoxidized soybean oil to substantially quantitative amounts of vicinal diesters while avoiding formation of the tetrahydrofuranyl (oxolane) ring structure.

U.S. Pat. No. 5,623,086 to Perri et al discloses a process for producing 1,2-bis(acyloxylates) that are useful with the invention.

BRIEF DESCRIPTION OF THE INVENTION

In a first embodiment the invention provides for a method for producing a lubricating oil including the steps of providing a renewable oil or fat such as vegetable or animal oil or fat; epoxidizing the oil or fat; and directly reacting the epoxidized oil or fat with a carboxylic acid anhydride, or a mixture of carboxylic anhydrides of selected chain lengths in the presence of basic catalysts to obtain the lubricating oil (triglyceride backbone diesters, hereafter referred to as diesters).

A second embodiment of the invention provides for a method for producing a lubricating oil including the steps of providing a vegetable or animal oil or fat; epoxidizing the oil or fat; hydrogenating the epoxidized oil or fat to obtain a hydrogenated intermediary having hydroxyl groups; and acylating the hydroxyl groups with an acylating agent, or mixtures of acylating agents of selected chain lengths to obtain the lubricating oil (triglyceride backbone monoesters, hereafter referred to as monoesters). An additional embodiment includes a method for producing a diester by providing an animal oil, animal fat, plant oil, or plant fat having an iodine number above about 7; epoxidizing said oil or fat; and reacting said epoxidized oil or fat with a carboxylic acid anhydride having between one and about 18 carbon atoms, in the presence of a basic catalyst, until essentially all of the epoxide functionality is reacted. Typically the basic catalyst comprises a tertiary amine such as triethylamine. In some embodiments interchain linkages are provided by control of the amount of anhydride in the reaction. In some embodiments two or more anhydrides are reacted to make a heterosubstituted diester.

Another embodiment includes a modified triglyceride heterosubstituted diester wherein adjacent carbon atoms originally joined by a double bond each have a pendant ester group and each of the ester groups is randomly selected from two or more different ester groups.

A yet further embodiment includes an industrial fluid comprising a modified triglyceride and another functional component such as a pour point depressant, anti-wear additive, base stock, diluent, extreme pressure additive, and/or antioxidant.

In some embodiments ester groups are provided that have at least one small ester group comprising from 2 to 17 carbon atoms is selected and at least one large ester group comprising from 3 to 18 carbon atoms is selected, and the ester groups differ by at least one carbon atom. Typically the ester groups are rendered different from one another by containing substituted heteroatoms selected from the group consisting of N, O, and P.

In some embodiments the ester groups are selected to have a number ratio of a large ester group to a small ester group that is ranges from about 0.1 to about 0.9. Typically the small ester group ranges from 2 to 5 carbon atoms and the large ester group ranges from 6 to 18 carbon atoms.

One embodiment provides for adjusting the viscosity of an industrial fluid by changing the difference between the number of carbon atoms in the smaller and larger of the two ester groups and/or changing the ratio of the amount of the smaller to the larger ester group.

A further embodiment provides for a method for making a modified triglyceride diester comprising providing an epoxydized triglyceride; reacting the epoxydized triglyceride with an acid anhydride in the presence of a basic catalyst to produce a diester; and separating the diester from the catalyst and unreacted anhydride. Typically the anhydrides two or more different anhydrides are reacted.

Another embodiment provides for a method for viscosity control of an industrial fluid by selecting a mixture of a short chain and longer chain anhydrides by controlling the ratio of short chain to long chain anhydrides, wherein small anhydrides when reacted provide 2 to 6 carbon atoms in a first ester and large anhydrides when reacted provide 6 to 18 carbon atoms in a second ester. Typically hydrolytic and/or thermal stability of the modified triglyceride is controlled by adding sterically hindering ester groups.

Another embodiment provides for a modified triglyceride monoester comprising: a modified triglyceride monoester having at least one set adjacent carbon atoms originally bound by a double bond wherein one originally double bond carbon has a hydrogen atom and the other carbon atom has a pendant ester group. A yet further embodiment provides for a modified triglyceride monoester comprising: a modified triglyceride monoester having at least two sets of adjacent carbon atoms originally bound by a double bond wherein one originally double bond carbon has a hydrogen atom and the other carbon atom has a pendant ester group and wherein the pendant ester group of one original double bond site is different from the ester group of the other original double bond site. Typically selected pendant ester groups are selected from the group consisting of acetate, isobuterate, hexanoate, and 2-ethylhexanaote. In some cases the modified diester triglyceride has ester groups that are different from one another by containing substituted heteroatoms selected from the group consisting of N, O, and P.

Another embodiment of the invention includes a method for making the modified triglyceride comprising: expoxidizing a triglyceride having at least one double bond; hydrogenating the expoxide group to generate mono-alcohols; and acylating the mono-alcohol with acid anhydride, acid chloride, or carboxylic acid. Typically the method includes acylating with a mixture of two or more different acylating agents to produce a triglyceride having different pendant ester groups.

Another embodiment includes a lubricant comprising: a mixture of triglycererides, wherein the mixture includes one or more triglycerides selected from the group consisting of Monoesters:

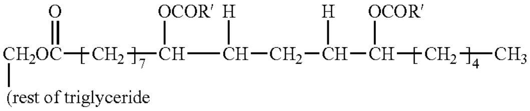

and

Diesters:

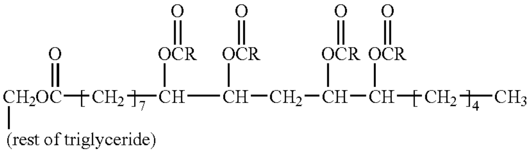

wherein R' and R are alkyl radicals, C1 to C18 and each R' may be the same or different, and each R may be the same or different, and mixtures thereof.

A yet further embodiment includes a method for producing a lubricant comprising: providing a plant or animal oil or fat, or a mixture thereof; epoxidizing said oil or fat; hydrogenating said epoxidized oil or fat to obtain a hydrogenated intermediary having hydroxylated arms; and acylating said hydroxylated arms with acylating agents of various chain lengths to obtain said lubricant.

Another embodiment includes a method of producing a lubricating oil comprising: providing an ester derived from a monool or polyol having at least one unsaturated site; epoxidizing said ester; and directly reacting said epoxidized ester with carboxylic acid anhydrides of varying chain lengths.

An additional embodiment includes a method of producing a lubricating oil comprising: providing an ester derived from a monool or polyol having at least one unsaturated site; epoxidizing said ester; hydrogenating said epoxidized ester to obtain a hydrogenated intermediary having hydroxylated arms, and acylating said hydroxylated arms with acylating agents of various chain lengths to obtain said lubricant.

A yet additional embodiment includes a lubricant composition comprising:

Monoesters:

a

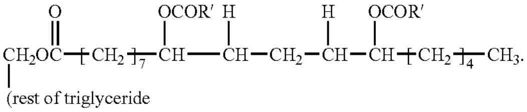

and/or

Diesters:

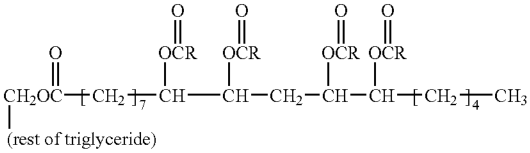

where R' and R includes alkyl groups varying from C1 to C18, cycloalkyl groups, aromatic groups, heterocyclic groups and mixtures thereof including a combination of different alkyl groups of different chain lengths within the same triglyceride molecule, and wherein each R' may be the same or different and each R may be the same or different.

DETAILED DESCRIPTION OF THE INVENTION AND BEST MODE

Figure 1:
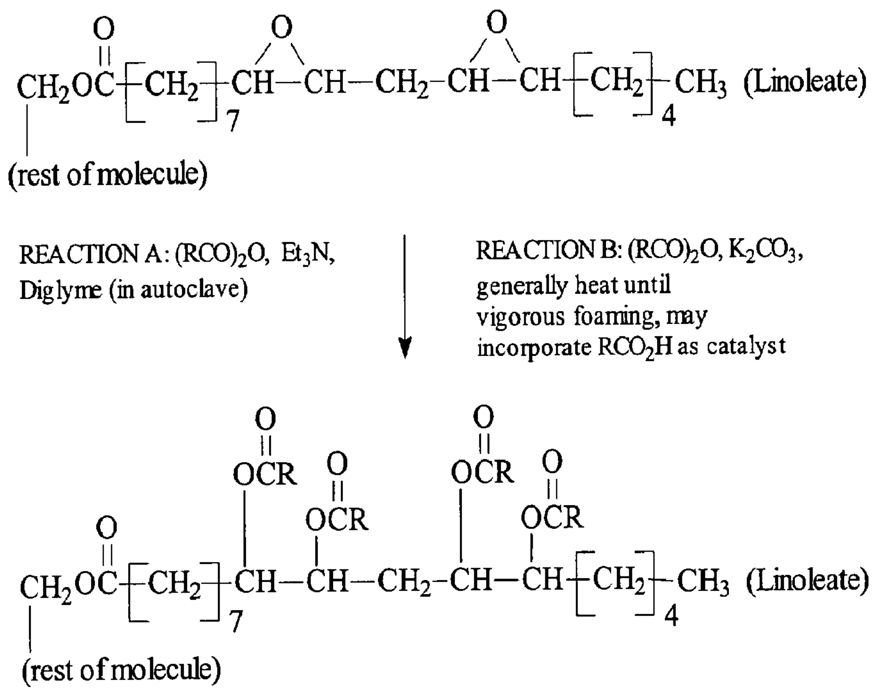
FIG. 1 illustrates two general routes for the preparation of vegetable or animal oil or fat diesters. The illustration specifically shows the preparation of soybean oil diesters from soybean oil via epoxidized soybean oil (ESO) by epoxide addition reactions.

The advantages of lubricating oils based on renewable sources such as vegetable and animal oils and fats include the following. The vegetable and animal oils or fats contain triglycerides having ester carbonyl groups. The polar nature of these ester carbonyl groups leads to strong adsorption on metal faces as a very thin film so that the film forming properties of triglyceride based lubricants are particularly advantageous in hydraulic systems. Vegetable oils and animal oils typically have high viscosity indices that facilitate their use over wide temperature ranges. Other advantages typically include high fume points (e.g. about 200° C.) and high flash points (e.g. about 300° C.).

Other advantages include the fact that vegetable and animal oil and fat based lubricants help reduce the depletion of fossil-derived hydrocarbons. Vegetable oil based lubricants are based on renewable resources and are typically biodegradable. The terms oils and fats are relative terms that are used interchangeably herein. Where the term oil is used it also includes fats and vice versa.

Oils useful with the invention include animal and plant oils having iodine numbers (I.N.) from the very low of about 7 (e.g. coconut oil) to about 160. Typical examples of useful oils include coconut oil (I.N.=6-11), palm oil (I.N.=50-55), olive oil (I.N.=75-88), canola oil (I.N.=100-115), menhaden oil (I.N.=115-160), soybean oil (I.N.=123-139), and safflower oil (I.N.=140-150). Among the soybean oils, mid oleic and high oleic soybean oils that are high in oleic acid are useful. The source oils and/or product oils may be mixed to provide unique properties to the final lubricating oil. Source oils may be refined, treated, and or mixed to obtain triglycerides having preferred properties in making the final product. Thus in some embodiments judicious selection of source triglycerides will provide selected properties for the final lubricating oil product.

Individual vegetable oils, including soybean oil, are triglycerides that contain characteristic quantities of individual fatty acids that are randomly distributed among these triglyceride structures. A typical soybean oil composition contains the following fatty acid composition: 11% palmitic acid, 4% stearic acid (both saturated), 54% linoleic acid (doubly unsaturated), 23% oleic acid (mono unsaturated), and 8% linolenic acid (triply unsaturated). While allylic methylene groups in triglyceride fatty acids such as oleic and especially doubly allylic methylene groups in triglyceride fatty acids such as linoleic and linolenic acids are susceptible to oxidation, the present invention overcomes this tendency by either adding two ester groups, (to form disesters) or adding an ester and a hydrogen atom (to form monoesters) to essentially all of the double bonds of triglyceride unsaturated fatty acids.

The specific orientation of such ester groups is such that an oxygen atom is attached directly to a carbon atom that originally was a component of a fatty acid double bond and a carbonyl group is attached to such oxygen atom. In addition to having enhanced oxidative stabilities, some of these derivatives may be characterized as advantageously having decreased pour points, increased responsiveness to pour point depressants, and increased (or a minimized decrease in) viscosity indices.

The oxidative instabilities of animal and vegetable oils result from attack of oxygen at the activated methylene groups flanking their numerous double bonds (e.g. soybean oil has approximately 4.7 double bonds per soybean triglyceride molecule). Especially vulnerable are these methylene groups flanked by two double bonds as found in linoleic and linolenic acids. One approach to improve these oils as lubricants is to add large quantities of various antioxidants to overcome their oxidative instability. On the other hand, modification or removal of these double bonds in the oils by processes such as hydrogenation significantly improves their oxidative stabilities but also leads to undesirable and very significant increases in pour points. The present invention modifies the double bonds in animal and vegetable oils and their derivatives in a manner that significantly increases their oxidative stabilities while maintaining, and in some cases improving upon, their pour points and viscosity profiles. Accordingly, a number of structurally diverse lubricant samples were prepared by the methods shown in FIGS. 1 and 2. In these figures "rest of molecule" refers to the rest of generalized triglycerides in a soy oil that typically contain a variety of fatty acids such as linoleic, oleic, linolenic and other fatty acids. The unsaturated fatty acids in the triglycerides are typically converted to diester or monoester derivatives.

A method to overcome hydrolytic and thermal attack is to incorporate sterically hindered ester groups into the modified triglyceride. Typical examples of sterically hindering ester groups include isobutyrate and 2-ethylhexanoate.

Referring now to FIG. 1, this figure shows one embodiment of the invention where epoxidized soybean oil is represented in the figure by an epoxidized linoleic fatty acid arm (since linoleic acid is the major fatty acid in soybean triglycerides). Other epoxide structures in these triglycerides can be derived from oleic and linolenic acid.

Referring again to FIG. 1, in Reaction A, in summary, epoxidized soybean oil, an acid anhydride {$(RCO)_2O$}, a tertiary amine such as triethylamine and diethyleneglycol dimethyl ether (diglyme) are heated in an autoclave for typically 15-20 hours to obtain soybean oil diesters. The same reaction would work for epoxidized propylene glycol disoyate, epoxidized methyl soyate, or other epoxidized fatty acid esters.

In FIG. 1, reaction B, in summary, epoxidized soybean oil, an acid anhydride $\{(RCO)_2O\}$, and anhydrous potassium carbonate are heated at temperatures up to approximately 210° C. until all epoxide functionality is consumed as indicated by proton nuclear magnetic resonance spectroscopy. In some cases, cessation of vigorous foaming indicates that this reaction is at or near completion. This reaction is expected to be applicable when the R group increases in size. Reactions A and B have both been used to prepare soybean oil diesters where R varies from C1 to $C_8$. The same reaction would work for epoxidized propylene glycol disoyate or epoxidized methyl soyate, or other epoxidized fatty acid esters.

Figure 2:
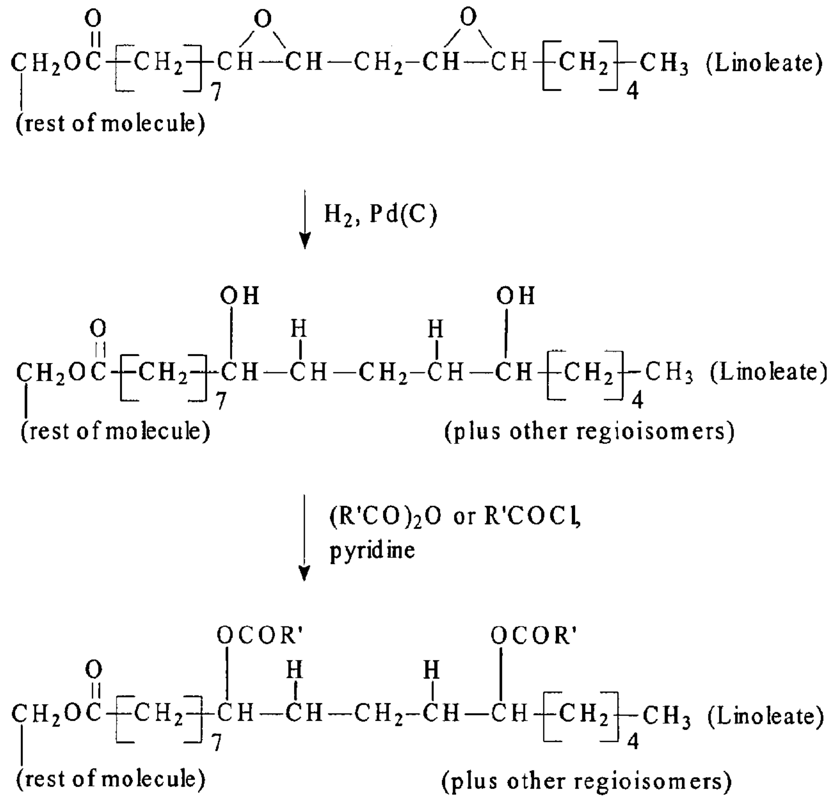
FIG. 2 illustrates a general route for the preparation of vegetable or animal oil or fat monoesters. The illustration specifically shows the preparation of soybean oil monoesters from soybean oil via epoxidized soybean oil by hydrogenation and acylation reactions.
Figure 3:
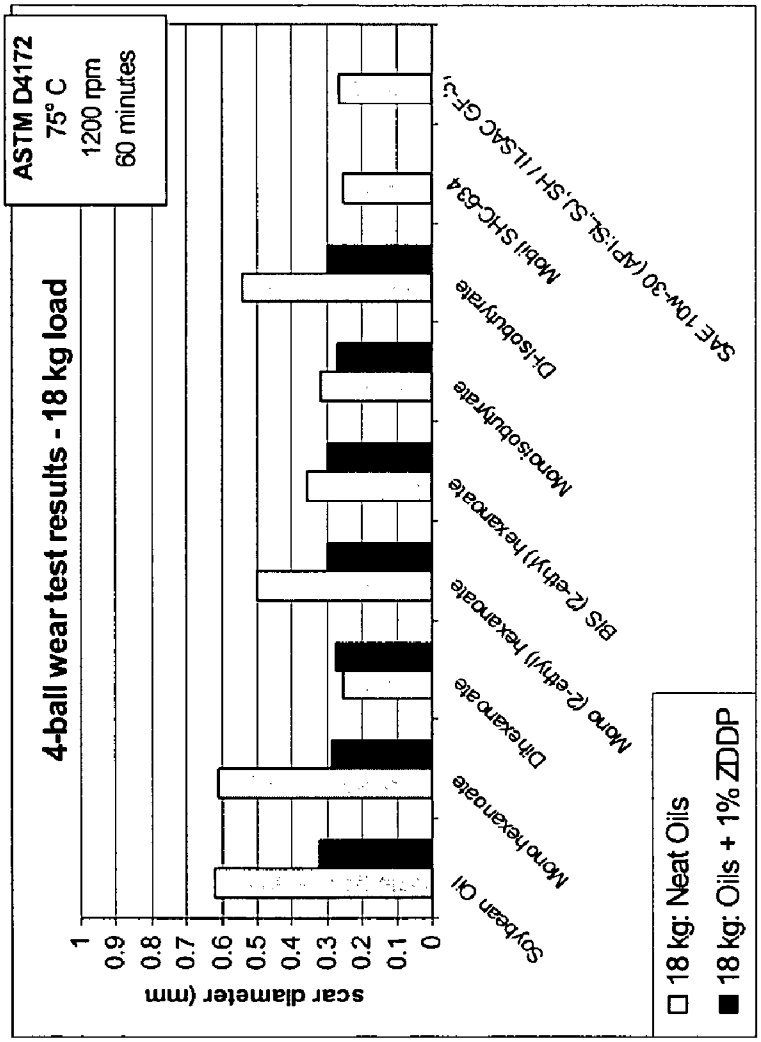
FIG. 3 illustrates a bar graph showing 18 kg load four ball wear test results for typical formulations.
Figure 4:
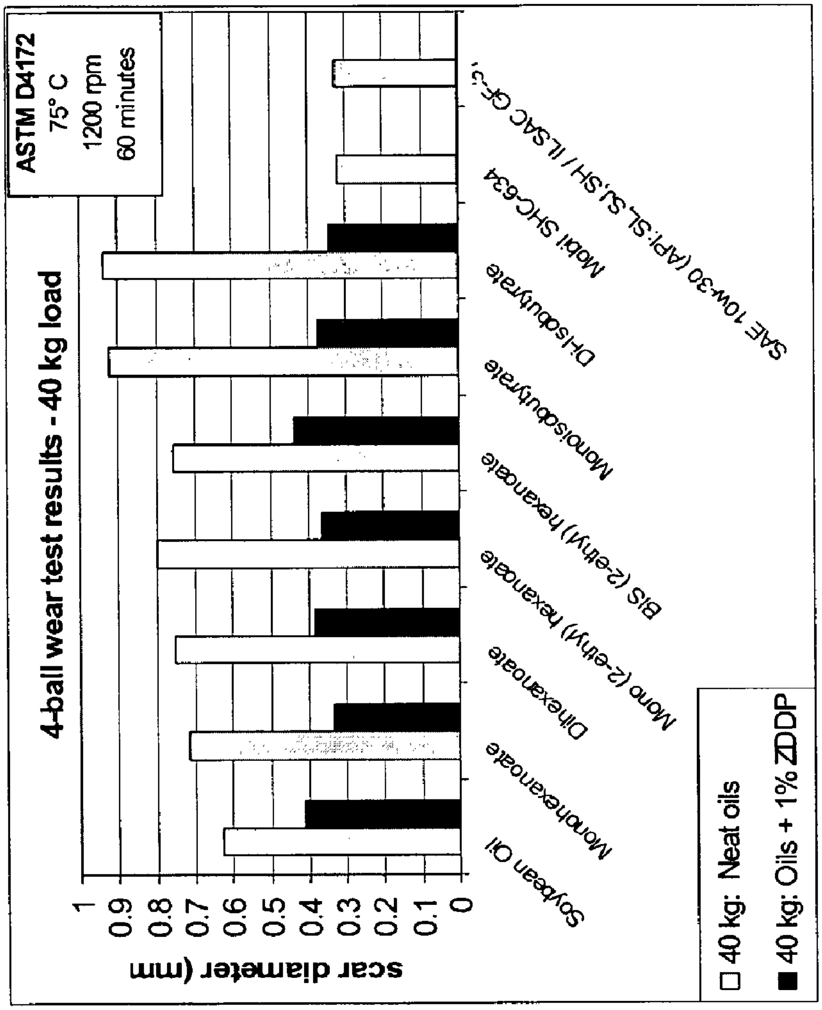
FIG. 4 illustrates a bar graph showing 40 kg load four ball wear test results for typical formulations and a soybean oil control.
Figure 5:
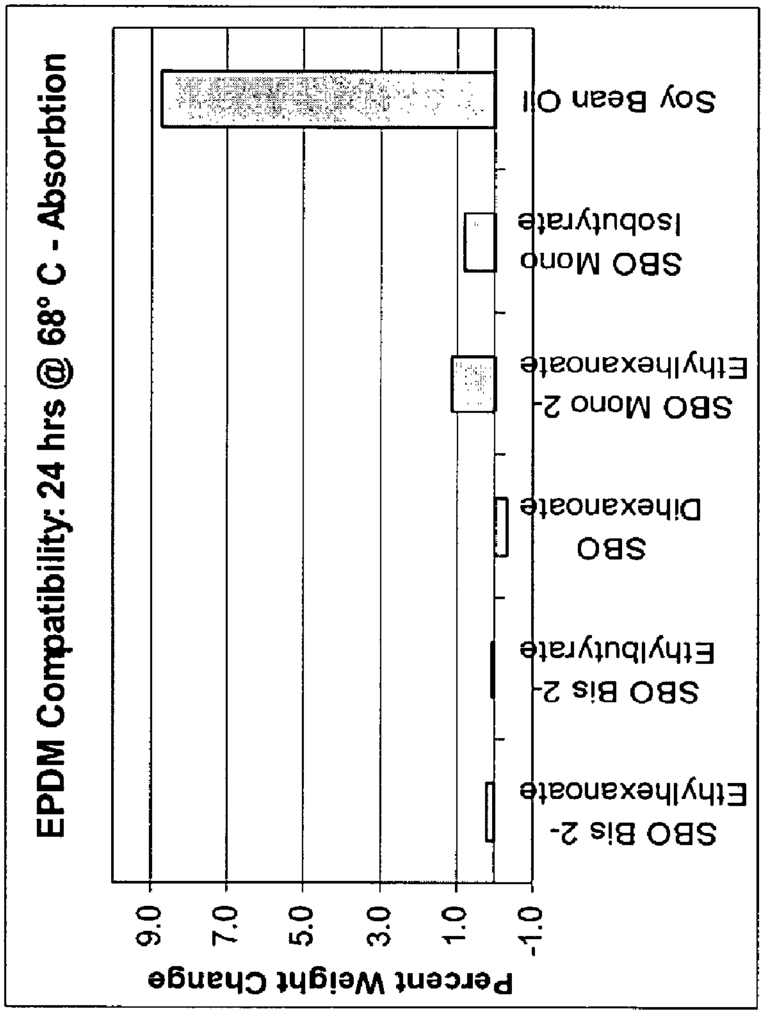
FIG. 5 illustrates a bar graph showing absorption test results of EPDM absorption compatibility for several typical formulations and a soybean oil control.
Figure 6:
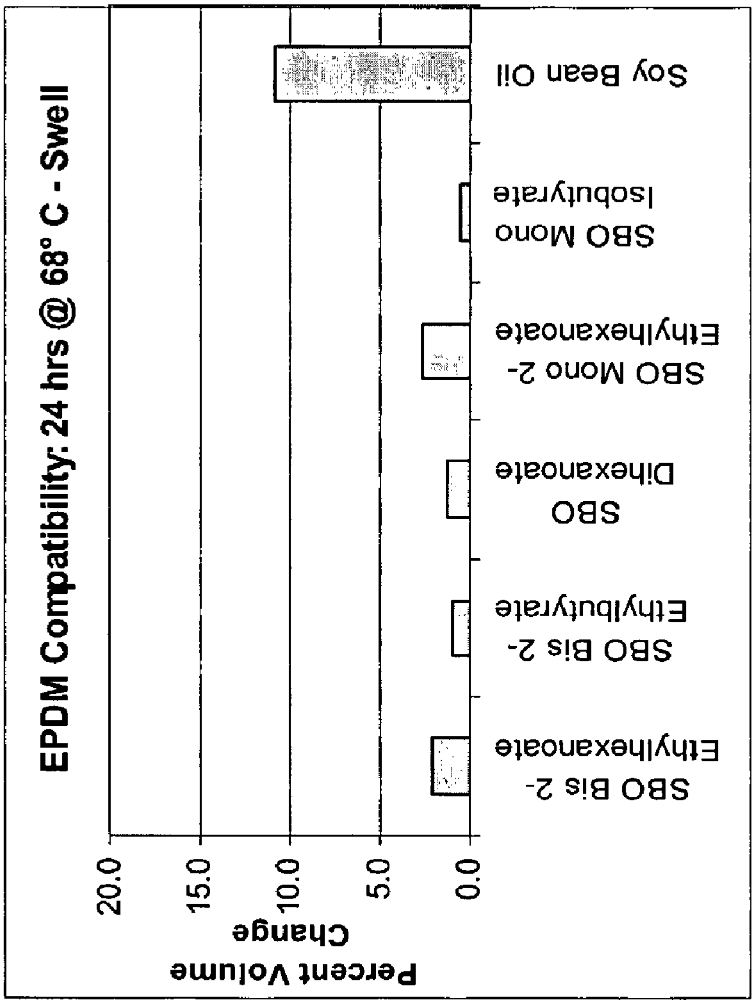
FIG. 6 illustrates a bar graph showing swell test results of EPDM compatibility for several typical formulations and a soybean oil control.
Figure 7:
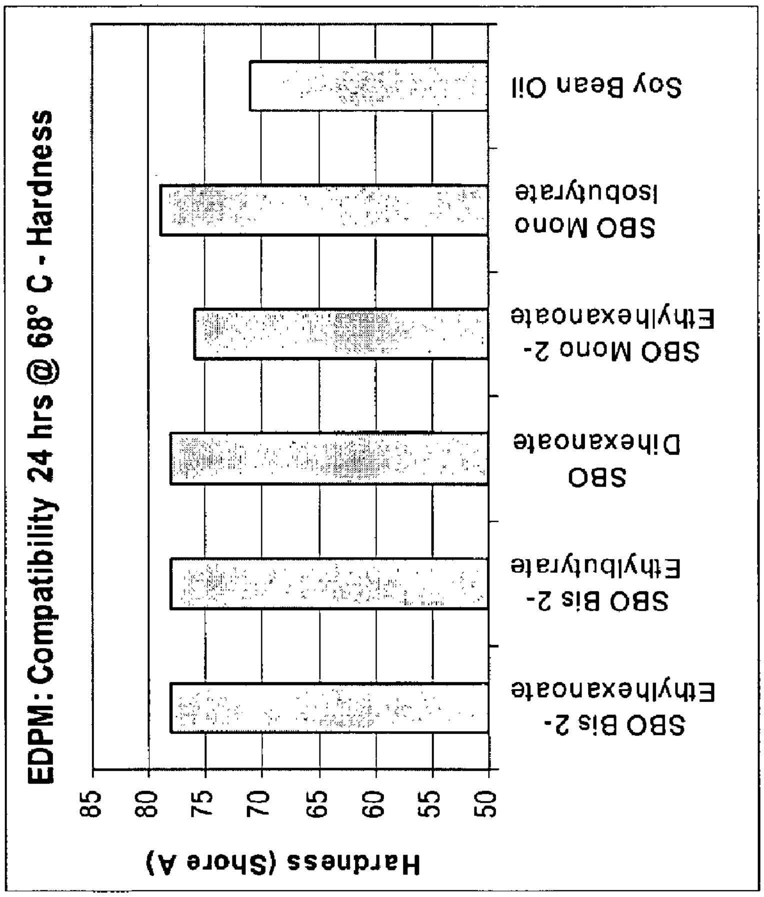
FIG. 7 illustrates a bar graph showing hardness test results of EPDM compatibility for several typical formulations and a soybean oil control.
Figure 8:
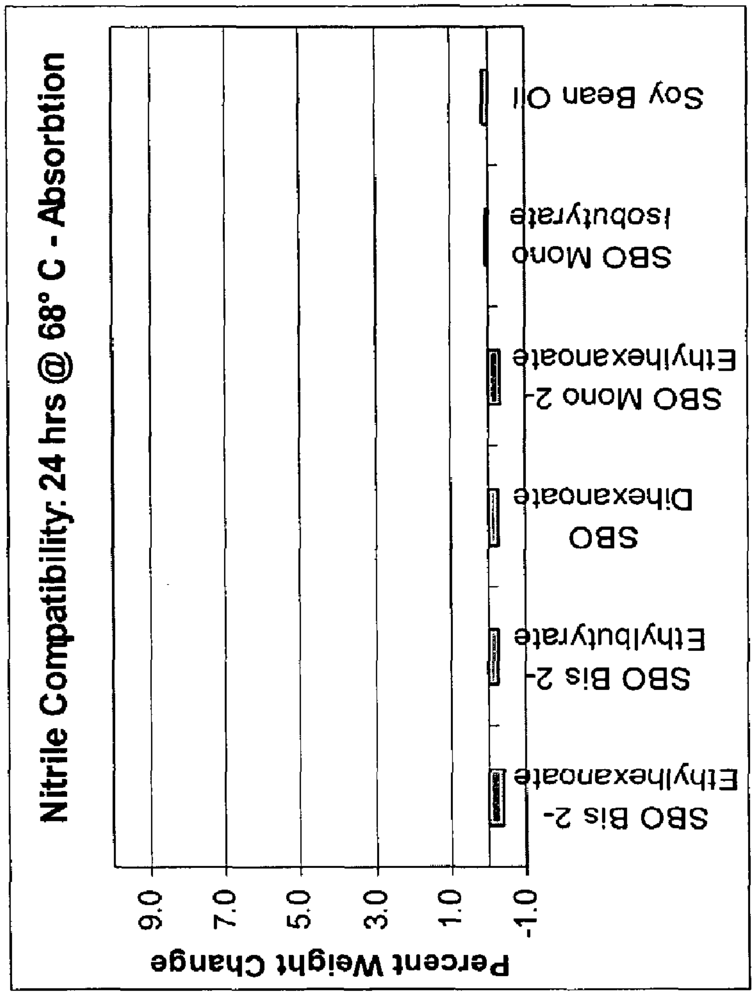
FIG. 8 illustrates a bar graph showing absorption test results of nitrile compatibility for several typical formulations and a soybean oil control.
Figure 9:
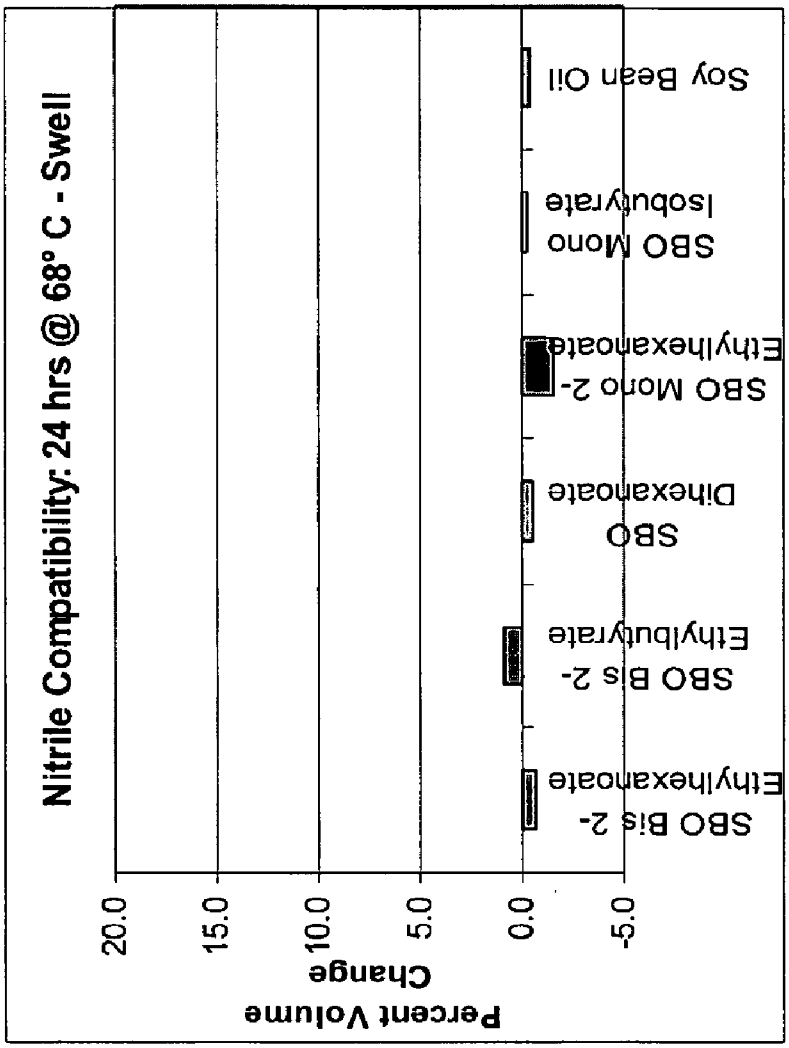
FIG. 9 illustrates a bar graph showing swell test results of nitrile compatibility for several typical formulations and a soybean oil control.
Figure 10:
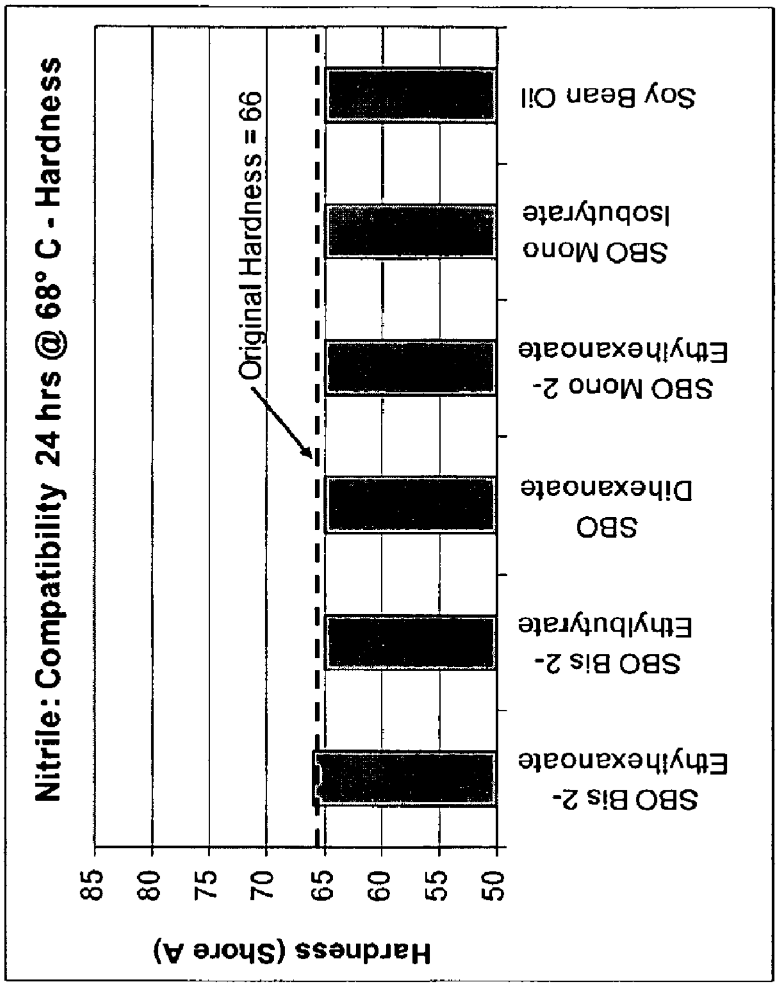
FIG. 10 illustrates a bar graph showing swell hardness test results of nitrile compatibility for several typical formulations and a soybean oil control.

The generalized approach shown in FIG. 2 involves the initial reduction of epoxidized soybean oil with typically hydrogen in the presence of a Pd(C), Pd $(Al_2O_2)$, Raney nickel or other hydrogenation catalysts. The hydrogenated material is then reacted by acetylation of the hydroxylated arms. As shown in FIG. 2, the hydrogenated epoxidized soybean oil is typically reacted with acylating agents such as acid anhydrides $\{(R'CO)_2O\}$ or acid chlorides (R'COCL) in the presence of acylating catalysts such as pyridine or hydrogen chloride traps such as triethylamine to obtain the end product. The same reaction sequence would work for epoxidized propylene glycol disoyate, epoxidized methyl soyate, or other epoxidized fatty acid esters.

The term "other regioisomers" in Formula 2 refers to the analogous structures resulting from the orientation of hydrogen atom and ester groups with reference to each other. In other words, each pair of ester groups and hydrogen atoms can have the orientations shown in Formula 2 or either or both can be exchanged with each other.

Performance tests were performed for soybean oil diesters and monoesters as described in Tables 1, 2 and 3.

Microoxidation tests were performed by the Penn. State microoxidation tests wherein oil samples (40 microliters) are placed on a stainless steel (C1010 steel) coupon, weighed, and then heated at 180° C. for variable amounts of time while 20 ml/minute dry air is passed over the heated sample for various lengths of time. The sample is weighed after heating and then washed with tetrahydrofuran to dissolve the oil while leaving behind deposits and the coupon is weighed again after complete removal of solvent to determine the amount of insoluble deposits. These analyses allow determination of the percent deposits and percent evaporation under these conditions.

It can be seen that in these micro-oxidation tests, the oils of the present invention generally gave much lower deposits and evaporation than refined, bleached and deodorized (RBD) soybean oil as well as high oleic soybean, which is known to be significantly more oxidatively stable than conventional soybean oil. RBD is a typical grade of soybean oil. Addition of anti-oxidants to the modified oils (mono and diesters) according to the present invention should lead to significantly improved oxidative stability compared to the oxidative stability achieved by addition of these additives to non-modified soybean oil itself.

All of the oils of the present invention had substantially higher viscosities than that of RBD soybean oil when measured at 40° C. and 100° C. There are needs in the lubrication industry to have oils with a range of viscosities enabling such oils to be used as base stocks or viscosity enhancers. Such oils will have even more utility since they are also shown to be biodegradable. It can also be advantageous for such an oil to have a higher viscosity index which indicates that such oil undergoes a lower change in viscosity when undergoing a set temperature change. Some oils of the present invention have viscosity indices which are similar to that of RBD soybean oil and one in particular (soybean oil monoisobutyrate) has a viscosity index that is significantly higher than that of soybean oil.

Numerous oils of the present invention had pour points similar to RBD soybean oil or advantageously lower than that of RBD soybean oil and also were receptive to having their pour points lowered by use of pour point depressants.

Two classes of lubricating oils according to the invention have been prepared: vegetable oil derived diesters (e.g. soybean oil diesters), where the diester is formed at the original double bonds of the unsaturated fatty acids; and vegetable oil derived monoesters (e.g. soybean oil monoesters). See the two formulas below.

Diesters:

Formula 1

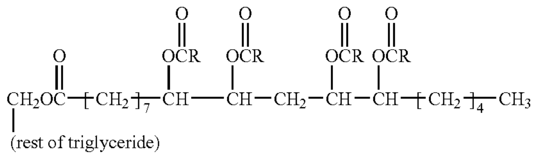

(rest of triglyceride typically includes diester derivatives of linoleic, oleic, linolenic, and other unsaturated fatty acids)

Monoesters:

Formula 2

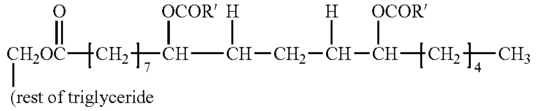

(plus other regioisomers)

(rest of triglyceride typically includes diester derivatives of linoleic, oleic, linolenic, and other unsaturated fatty acids)

The R— and R' groups of Formulas 1 and 2 may be the same or different and are typically alkyl groups having one to 18 carbon atoms. More preferably, the R groups may be the same or different and typically contain from about one to about eight carbon atoms. In some embodiments R may be the same or different and may include one or more aromatic groups and substituted aromatic groups. In some embodiments at least one of the R groups is different and such material will originate by using a mixture of two or more different acylating reagents when either of the two approaches are applied.

Advantageously, the diester preparation methods described herein also provide for diester triglycerides having interchain ether linkages between different fatty acid arms (chains) in the same triglyceride molecule and/or between fatty acid arms in different triglyceride molecules. Typically about 0 to about 4 intrachain or interchain ether linkages are generated for every 100 ester groups that become attached to the triglyceride structure when prepared with Reaction B of FIG. 1. The existence of the aforementioned ether linkages is based on interpretation of NMR data. The advantage of these ether linkages is to provide control of properties for the molecule and to any formulations to which it is added (e.g. viscosity, stability). The number of interchain ether linkages is controlled by the relative amount of anhydride used in the reactions. A higher amount of anhydride for example is expected to reduce the number of interchain linkages while a lesser amount of anhydride is expected to increase the number.

Referring again to Formulas 1 and 2, typically, for soybean oil derived diesters there are about 3.1 ester groups per fatty acid arm (average of 1.55×2). Typically, for soybean oil derived monoesters there are about 1.55 ester groups per fatty acid arm. Placement of ester functionality in diesters and monoesters along their fatty acid arms is expected to increase their adsorption to metals and their film forming properties.

In one embodiment of the invention the general strategy in synthesizing the lubricants was to attach alkyl groups (R) with increasing size and also incorporate branching in the backbone diester and monoester series. The 2-ethylhexanoic and the 2-ethylbutyric ester groups were attached to the fatty acid backbones due to the reported high thermal and hydrolytic stability of these specific esters.

Steam deodorization was used for some examples herein. It is a process commonly used in the natural oil industry to remove fatty acids, monoglycerides and other materials that will volatilize and distil with the aid of a steam flow. This process has been employed to purify both diesters and monoesters in the present invention and is an alternative to heating reaction mixtures with mixtures of pyridine and water to hydrolyze recalcitrant acid anhydrides and acid chlorides. The steam flow advantageously converts both acid anhydrides and acid chlorides to their corresponding acids, while not hydrolyzing the triglyceride ester linkages. In the laboratory-scale steam deodorization approach used in the present invention, crude reaction mixtures were placed in a round bottom deodorization flask attached to a condenser and receiver flask that was maintained under negative pressure with a vacuum pump. In the examples that used this step, the reaction flask was also connected to a water/steam reservoir via non-collapsible tubing and the steam inlet was directed beneath the surface of the reaction mixture in the deodorization flask. The water/steam reservoir was heated to various temperatures to partially control the steam influx.

The following examples are intended to be illustrative of the invention and are not meant to limit the scope of the invention in any way.

Example 1

This example illustrates the preparation of soybean oil diacetate prepared from the reaction of epoxidized soybean oil with acetic anhydride using triethylamine as a catalyst in the presence of diglyme in an autoclave, according to FIG. 1, Reaction A. In one reaction, 11.27 g epoxidized soybean oil (0.049 mole epoxide), 6.32 g acetic anhydride (0.062 mole), triethylamine (0.55-0.7 mL), diglyme (0.5 mL) were heated in an autoclave at approximately 125° C. for 22 hours to obtain a quantitative conversion to soybean oil diacetate. The progress of this type reaction was followed by proton nuclear magnetic resonance (NMR) spectroscopy. Residual acetic anhydride was removed by distillation in a short path distillation apparatus. The residue was dissolved in 150 mL ethyl ether, extracted with water and the ether layer was dried over magnesium sulfate. The solvent was removed in a rotary evaporator to obtain 12.69 g of an oil. A sample (sample 1) prepared by this method was tested and retested at a later time (sample 1A) as shown in Table 1. Another sample of soybean oil diacetate (sample 2) was prepared in a manner similar to that described above and test results are also shown in Table 1.

Example 2

This example describes the preparation of soybean oil bis (2-ethylhexanoate) prepared from the reaction of epoxidized soybean oil with 2-ethylhexanoic anhydride using triethylamine as a catalyst in the presence of 2-ethylhexanoic acid and diglyme in an autoclave, according to FIG. 1, Reaction A. In one reaction, 74.99 g epoxidized soybean oil (0.328 mole epoxide), 111.37 g 2-ethylhexanoic anhydride (0.412 mole), 11.69 g 2-ethylhexanoic acid (0.081 mole), 2.69 g triethylamine (0.027 mole), 3.12 g diglyme were heated in an autoclave at approximately 150° C. for 20 hours to obtain complete conversion to soybean oil bis(2-ethylhexanoate). Residual 2-ethylhexanoic anhydride, 2-ethylhexanoic acid, triethylamine and diglyme were removed by vacuum distillation with a Kugelrohr short-path distillation apparatus. NMR analysis indicated that residual epoxidized soybean oil, 2-ethylhexanoic anhydride, 2-ethylhexanoic acid, triethylamine and diglyme were not present in this oil.

Examples 3-7 illustrate the preparation of homosubstituted soybean oil diesters prepared from the reaction of epoxidized soybean oil with different acid anhydrides in the presence of potassium carbonate at elevated temperatures as shown in general in FIG. 1, Reaction B.

Example 3

This example describes the preparation of soybean oil dipropionate. Epoxidized soybean oil (50.0 g, approximately 0.219 mole epoxide), 34.7 mL propionic anhydride (0.263 mole) and 3.067 g anhydrous potassium carbonate were dispensed in an argon filled glove bag and added to a 250 mL three-necked flask equipped with heating mantle, magnetic stirring, condenser with argon gas inlet tube, and thermocouple residing in the reaction mass. After flushing the flask with argon, the reaction mixture was maintained under an argon atmosphere by means of a bubbler device. The rheostat controlling the heating mantle was set at an intermediate setting which allowed the temperature of the reaction contents to rise to approximately 206° C. after approximately four hours. The reaction mixture was maintained at this temperature for another two hours at which time proton NMR analysis indicated that all epoxide functionality had been consumed. The reaction mixture was allowed to cool overnight and was heated to 42° C. to convert it to a liquid. This mixture was transferred to a separatory funnel by addition of 2×100 mL portions of ethyl ether and the combined ether solution was washed with 100 mL water washes until the pH of the washes minimized at pH 4 and did not change further. This wash removes the potassium carbonate while not removing excess propionic anhydride. The ether solution was passed through cotton, dried over sodium sulfate and the ether solution was stripped in a rotary evaporator with a bath temperature at 50° C. under aspirator pressure and then at approximately 0.4 Torr with a vacuum pump. This mixture was heated at 60-70° C. with magnetic stirring for 2 hours with 30 mL water and 10 mL pyridine to hydrolyze excess propionic anhydride to propionic acid. This mixture was transferred to centrifuge tubes with 200 mL ethyl acetate and rapidly shaken with 100 mL of wash solutions to obtain mixtures that were phase separated by centrifugation, after which the lower aqueous phases were removed by pipette. The following solutions were used: water (pH 6), 10% sodium hydroxide (pH 10), 10% sodium hydroxide (pH 14), 10% hydrochloric acid and added another 100 mL ethyl acetate (pH 1), 5% sodium bicarbonate (pH 9), water (pH 8), water (pH 7), water (pH 5), water (pH 5), water (pH 5). The ethyl acetate solution was filtered through cotton, dried over sodium sulfate, and stripped in a rotary evaporator under aspirator pressure with a bath temperature of 41° C. and then at 0.3 Torr with a vacuum pump with a bath temperature of 50° C. for 2.3 hours to obtain 64.7 g of an oil. NMR and infrared (IR) spectral analysis indicated that residual epoxy and hydroxyl functionality and propionic anhydride were not present in this oil.

Example 4

This example illustrates the preparation of soybean oil diisobutyrate. Epoxidized soybean oil (50.0 g, approximately 0.219 mole epoxide), 45.0 mL isobutyric anhydride (0.263 mole) and 3.027 g anhydrous potassium carbonate were dispensed in an argon filled glove bag and added to a 250 mL three-necked flask equipped with heating mantle, magnetic stirring, condenser with argon gas inlet tube, and thermocouple residing in the reaction mass. After flushing the flask with argon, the reaction mixture was maintained under an argon atmosphere by means of a bubbler device. The rheostat controlling the heating mantle was set at an intermediate setting which allowed the temperature of the reaction contents to rise to approximately 210° C. after approximately 55 minutes after which the mixture was allowed to slowly cool. Proton NMR analysis of a sample taken after 70 minutes indicated that all epoxide functionality had been consumed. The reaction mixture was allowed to cool overnight and was then warmed with 100 mL ethyl ether and transferred to a separatory funnel using an additional 100 mL portion of ethyl ether as a rinse. The combined ether solution was washed with 100 mL water washes until the pH of the washes minimized at pH 4 and did not change further. These mixtures were centrifuged due to very slow phase separation. This wash removes potassium carbonate but does not remove excess isobutyric anhydride. The ether solution was passed through cotton, dried over sodium sulfate and the ether solution was stripped in a rotary evaporator with a bath temperature at 50° C. under aspirator pressure and then at approximately 0.5 Torr with a vacuum pump for 3.5 hours. This mixture was heated at 60-70° C. with magnetic stirring for 2.3 hours with 30 mL water and 10 mL pyridine to hydrolyze excess isobutyric anhydride to isobutyric acid. This mixture was transferred to centrifuge tubes with 200 mL ethyl acetate and rapidly shaken with 100 mL of wash solutions to obtain mixtures that were phase separated by centrifugation, after which the lower aqueous phases were removed by pipette. The following solutions were used: water (pH 6), 10% sodium hydroxide (pH 10), 10% sodium hydroxide (pH 10), 10% hydrochloric acid and added another 100 mL ethyl acetate (pH 1), 5% sodium bicarbonate (pH 9), water (pH 8), water (pH 8), water (pH 5), water (pH 5), water (pH 5). The ethyl acetate solution was filtered through cotton, dried over sodium sulfate, and stripped in a rotary evaporator under aspirator pressure with a bath temperature of 41° C. and then at 0.3 Torr with a vacuum pump with a bath temperature of 50° C. for three hours to obtain 56.1 g of an oil. NMR and infrared (IR) spectral analysis indicated that residual epoxy and hydroxyl functionality and isobutyric anhydride were not present in this oil.

Example 4A

Preparation of Soybean Oil Diisobutyrate According to FIG. 1, Reaction A

This example illustrates the preparation of soybean oil diisobutyrate according to FIG. 1, Reaction A. The following were charged into a 300 mL stirring autoclave: 45.86 g epoxidized soybean oil (0.2006 mole epoxide), 39.14 g isobutyric anhydride (0.2474 mole), 4.30 g isobutyric acid (0.0488 mole), 1.64 g triethylamine (0.0162 mole), and 1.91 g diethyleneglycol dimethyl ether (diglyme; 0.0142 mole). The autoclave was cycled between 100 psi argon and atmospheric pressure three time to flush the air from the autoclave and the autoclave was then pressurized to 100 psi with argon. Use of the carboxylic acid corresponding to the acid anhydride had been shown in the preparation of soybean oil diacetate to accelerate the diacylation reaction and give reproducible results. The autoclave was stirred at 300 RPM and the contents were heated 20 hours at which time all epoxy functionality was shown to be completely consumed by proton NMR spectroscopy based on the absence of absorptions in the 2.9-3.1 ppm region. The reaction mixture was transferred to a round bottom flask and the volatile components were removed in a Kugelrohr apparatus by initially heating at 100° C. for one hour at a pressure of approximately 0.06 Torr and then heating at 140° C. for 5.5 hours at a pressure of approximately 0.05 Torr to obtain 69.99 g yellow, moderately viscous liquid. The proton NMR spectrum of this material had absorptions at 4.80-5.35 ppm corresponding to the two methine hydrogen atoms originally attached to the epoxy functionality that each became attached to isobutyrate groups and integration of these signals indicated nearly complete diacylation. The IR spectrum had a strong absorption at 1737 $cm^{-1}$ corresponding to the isobutyrate ester groups.

Example 5

This example illustrates the preparation of a soybean oil derived bis(2-ethylbutyrate). Epoxidized soybean oil (25.0 g, approximately 0.110 mole epoxide), 28.18 g bis(2-ethylisobutyric) anhydride (0.132 mole) and 1.520 g anhydrous potassium carbonate were dispensed in an argon filled glove bag and added to a 250 mL three-necked flask equipped with heating mantle, magnetic stirring, condenser with argon gas inlet tube, and thermocouple residing in the reaction mass. After flushing the flask with argon, the reaction mixture was maintained under an argon atmosphere by means of a bubbler device. The rheostat controlling the heating mantle was set at an intermediate setting which allowed the temperature of the reaction contents to rise to approximately 203° C. after approximately 64 minutes. The temperature slowly decreased to 198° C. after 93 minutes at which time proton NMR analysis that all epoxide functionality had been consumed. Very little foaming was noted during the course of this reaction. The reaction mixture was allowed to cool overnight and was then warmed with 25 mL ethyl ether and transferred to a separatory funnel using an additional 25 mL portion of ethyl ether as a rinse. The combined ether solution was washed with 50 mL water washes until the pH of the washes minimized to pH 4, after addition of an additional 50 mL ethyl ether, and did not change further. This wash removes potassium carbonate but does not remove excess bis(2-ethylbutyric) anhydride. The ether solution was passed through cotton, dried over sodium sulfate and the ether solution was stripped in a rotary evaporator with a bath temperature at 43° C. under aspirator pressure. This mixture was heated at approximately 60° C. with magnetic stirring for two hours with 15 mL water and 5 mL pyridine to hydrolyze excess bis(2-ethylbutyric) anhydride to isobutyric acid. This mixture was transferred to centrifuge tubes with 50 mL ethyl acetate and rapidly shaken with 100 mL of wash solutions to obtain mixtures that were phase separated by centrifugation, after which the lower aqueous phases were removed by pipette. The following solutions were used: water (pH 6), 10% sodium hydroxide (pH 10), 10% sodium hydroxide (pH 14), 10% hydrochloric acid and added additional 100 mL ethyl acetate (pH 0), 5% sodium bicarbonate (pH 9), water (pH 7), water (pH 6), water (pH 5), water (pH 5). After adding another 100 mL ethyl acetate, this solution was filtered through cotton, dried over sodium sulfate, and stripped in a rotary evaporator under aspirator pressure with a bath temperature of 41° C. and then at 0.5 Torr with a vacuum pump with a bath temperature of 50° C. for four hours to obtain 37.9 g of an oil. NMR and infrared (IR) spectral analysis indicated that residual epoxy and hydroxyl functionality and bis(2-ethylbutyric) anhydride were not present in this oil.

Example 6

This example illustrates the preparation of soybean oil dihexanoate. Epoxidized soybean oil (50.0 g, approximately 0.219 mole epoxide), 61.47 mL hexanoic anhydride (0.263 mole) and 3.032 g anhydrous potassium carbonate were dispensed in an argon filled glove bag and added to a 250 mL three-necked flask equipped with heating mantle, magnetic stirring, condenser with argon gas inlet tube, and thermocouple residing in the reaction mass. After flushing the flask with argon, the reaction mixture was maintained under an argon atmosphere by means of a bubbler device. The rheostat controlling the heating mantle was set at an intermediate setting which allowed the temperature of the reaction contents to rise to approximately 236° C. after approximately 65 minutes after which the mixture cooled to 217° C. after 93 minutes without decreasing the rheostat setting (indicating an exotherm had occurred). Significant foaming was noted when the reaction mixture reached approximately 150° C. Proton NMR analysis of a sample taken after 65 minutes indicated that all epoxide functionality had been consumed at that time. The reaction mixture was allowed to cool overnight and was then warmed with 50 mL ethyl ether and transferred to centrifuge tubes with additional 50 mL portion of ethyl ether used as a rinse. All subsequent washing required centrifugation to obtain effective phase separation. The combined ether solution was washed with 50 mL water washes until the pH of the washes minimized to pH 4 and did not change further with continued water washing. This wash removes potassium carbonate but does not remove excess hexanoic anhydride. The ether solution was passed through cotton, dried over sodium sulfate and the ether solution was stripped in a rotary evaporator with a bath temperature at 43° C. under aspirator pressure. This mixture was heated at approximately 60° C. with magnetic stirring for 2 hours with 30 mL water and 10 mL pyridine to hydrolyze excess hexanoic anhydride to hexanoic acid. This mixture was transferred to centrifuge tubes with 100 mL ethyl acetate and rapidly shaken with 100 mL of wash solutions to obtain mixtures that were phase separated by centrifugation, after which the lower aqueous phases were removed by pipette. The following solutions were used: water (pH 6), 10% sodium hydroxide (pH 10), 10% sodium hydroxide (pH 14), 10% hydrochloric acid (pH 0), 5% sodium bicarbonate (pH 9), water (pH 7), water (pH 6), water (pH 5), water (pH 5). After adding another 100 mL ethyl acetate, this solution was dried over sodium sulfate, and stripped in a rotary evaporator under aspirator pressure with a bath temperature of 50° C. and then at 0.3 Torr with a vacuum pump with a bath temperature of 50° C. for 4 hours to obtain 65.6 g of an oil. NMR and infrared (IR) spectral analysis indicated that residual epoxy and hydroxyl functionality and hexanoic anhydride were not present in this oil.

Example 6A

Soybean Oil Dihexanoate Using Steam Deodorization Process for Removal of Acid Anhydrides or Acid Chlorides

Ex. 6 Describes the Use of Pyridine/Water to Remove Excess Hexanoic Anhydride Steam deodorization was used to purify 221.7 g of a crude reaction mixture of soybean oil dihexanoate that had been prepared using the same procedure described in Example 6 but before treatment with pyridine and water to remove hexanoic anhydride. This material had a starting acid value of approximately 22. Water vapor was not initially passed through the sample maintained at ambient temperature as the pressure was reduced to 0.5 Torr due to significant foaming. As the foaming subsided, the temperature was increased to 193° C. and the pressure reduced to 0.2 Torr while allowing introduction of steam through the system over a four hour period after which the temperature was increased to 240° C. but significant material was being lost to foaming. The acid value of the reaction mixture had decreased to 0.47 and 21% of its mass had distilled at this point. After an additional 1.5 hours at 245-250° C. and 0.1-0.15 Torr with increasing steam throughput, the acid value had decreased to 0.08. In an attempt to decrease the acid value even lower, the mixture was maintained for 2.5 hours at the same temperature and pressure to obtain a material with acid value of 0.06. The percent mass recovery at this point was only 58% and the acid value had been decreased to 0.06 and the material was passed through a bed of diatomaceous earth to remove trace stopcock grease. The loss of material lost due to significant foaming can be decreased by modification of the deodorization equipment to minimize such foaming. However, it is likely that soybean diester was also lost due to its distillation as was determined in the steam distillation of soybean oil bis(2-ethylhexanoate) as described below by using infrared analysis of the steam deodorization distillate. Thus, effective steam deodorization requires that the process be modified or stopped in order to remove most acidic components before soybean oil ester product also distils.

Example 7

This example illustrates the preparation of soybean oil bis(2-ethylhexanolate). Epoxidized soybean oil (25.0 g, approximately 0.110 mole epoxide), 35.06 g bis(2-ethylhexanoic) anhydride (0.1315 mole) and 1.5295 g anhydrous potassium carbonate were added to a 250 mL three-necked flask equipped with heating mantle, magnetic stirring, condenser with argon gas inlet tube, and thermocouple residing in the reaction mass. After flushing the flask with argon, the reaction mixture was maintained under an argon atmosphere by means of a bubbler device. The rheostat controlling the heating mantle was set at an intermediate setting which allowed the temperature of the reaction contents to rise to approximately 212° C. after 60 minutes. The reaction mixture was increased to 227° C. after 76 minutes but NMR analysis of the reaction mixture obtained after 60 minutes indicated complete consumption of epoxide functionality at that time. The reaction mixture was allowed to cool overnight and was gently heated with 50 mL ethyl ether to partially dissolve the mixture and transferred to a separatory funnel using another 50 mL of rinse ether. This mixture was washed with 50 mL water washes until the pH of the washes was reduced to 4.5. This wash removes the potassium carbonate while not removing excess bis(2-ethylhexanoic) anhydride. The ether solution was passed through cotton, dried over sodium sulfate and the ether solution was stripped in a rotary evaporator with a bath temperature at 50° C. under aspirator pressure. This mixture was heated at 65° C. with magnetic stirring for 2 hours with 15 mL water and 5 mL pyridine to hydrolyze excess bis(2-ethylhexanoic) anhydride to bis(2-ethylhexanoic) acid. This mixture was transferred to centrifuge tubes with 50 mL ethyl acetate and rapidly shaken with 50 mL of wash solutions to obtain mixtures that were phase separated by centrifugation, after which the lower aqueous phases were removed by pipette. The following solutions were used: water (pH 6.5), 10% sodium hydroxide (pH 9), 10% sodium hydroxide (pH 10), 10% hydrochloric acid (pH 0), 5% sodium bicarbonate (pH 9), water (pH 6), water and an additional 50 mL ethyl acetate (pH 6), water (pH 5), water (pH 5). The ethyl acetate solution was filtered through cotton, dried over sodium sulfate, and stripped in a rotary evaporator under aspirator pressure with a bath temperature of 46° C. and then at 0.5 Torr with a vacuum pump to obtain 45.6 g of an oil. However, NMR and infrared (IR) spectral analysis indicated that residual anhydride was still present in this oil apparently due to the high steric congestion about the anhydride carbonyl groups. Thus, the above procedure for anhydride hydrolysis with water/pyridine was repeated but the mixture was heated 190 minutes and this mixture was then transferred to a separatory funnel with 200 mL ethyl acetate. This mixture was washed with the following wash solutions and the following pH values were obtained: water (pH 6.5), 10% sodium hydroxide (pH 13), 10% sodium hydroxide (pH 12), 10% hydrochloric acid (pH 0-1), 5% sodium bicarbonate (pH 8.5), water and an additional 55 mL ethyl acetate (pH 7), water (pH 5.5), water and an additional 50 mL ethyl acetate (pH 5.5). The ethyl acetate solution was filtered through cotton, dried over sodium sulfate, and stripped in a rotary evaporator under aspirator pressure with a bath temperature of 50° C. and then with a vacuum pump to obtain 41.0 g of an oil. The NMR spectrum of this material indicated spectral analysis indicated that no residual bis(2-ethylhexanoic) anhydride was present in this oil.

Example 7A

Steam deodorization was used to purify 398.6 g of a crude reaction mixture of soybean oil bis(2-ethylhexanoate) that had been prepared in two batches using the same procedure described in Example 7 but before treatment with pyridine and water to remove bis(2-ethylhexanoic) anhydride. This material had a starting acid value of 12.86. The temperature of the reaction mixture was initially raised to 210° C. at 0.1 Torr without steam flow at which point the water vapor flow was slowly increased until the temperature reached 250° C. The distillate density collected at higher pot temperatures was much higher than initially collected which indicates that product diester is being distilled at that time. The weight of the reaction mixture at this stage was 329.7 g which corresponds to a 17.5% weight loss, whereas the predicted weight loss based on the amount of excess acid anhydride was about 9.7%. The acid value at this stage was 0.37. The steam deodorization was continued while increasing the steam content compared to that used in the first stage and another 9.6% of material was distilled. However, the fact that the acid value of this material was 0.38 indicates that all excess anhydride had been effectively removed during the first stage. The reaction mixture was passed through a diatomaceous earth bed to remove trace stopcock grease. Infrared analysis of the first stage distillate indicated anhydride, ester and acid peaks at 1813, 1737, and 1708 $cm^{-1}$, respectively, the second stage distillate was mainly ester, indicating that soybean oil bis(2-ethylhexanoate) can also be steam distilled under these conditions. Thus, effective steam deodorization requires that the process be stopped appropriately before product lubricants also distil.

Examples 8-14 illustrate the preparation of soybean oil monoesters formed by the hydrogenation of epoxidized soybean oil and acylation of this product with either acid anhydrides or acid chlorides. Hydrogenation of epoxidized soybean oil was performed in a Paar shaking hydrogenation apparatus. In a typical example, 29.4 g 10% palladium on carbon was placed in a 2.5 L Paar bottle previously sparged with argon and a solution of 164.8 g of epoxidized soybean oil (Vikoflex 7170, oxirane number 7.0) in a mixture of 751 ml ethanol and 40 ml glacial acetic acid was added. The bottle was attached to the hydrogenation apparatus and subjected to six cycles of compressing to 60 psi hydrogen and releasing to near atmospheric pressure. The hydrogen pressure was maintained close to 50-60 psi and the reaction proceeded for approximately 8 days at which time there was minimal further decrease in bottle pressure with the bottle isolated from the reservoir hydrogenation tank. The reaction mixture was filtered through a pad of diatomaceous earth using rinse glacial ethanol and this solution was lyophilized under high vacuum to obtain 112.0 g of a white solid. Proton NMR spectroscopy indicated complete consumption of epoxide functionality and also indicated a low level of mono- and diglycerides formed.

Example 8

This example illustrates the preparation of soybean oil monoacetate according to FIG. 2. Hydrogenated epoxidized soybean oil (23.43 g, 0.104 mole hydroxyl group) was reacted with 352 mL acetic anhydride (3.73 mole) and 11.7 mL pyridine in a 1 L flask equipped with a magnetic stirrer and heated at 60° C. for 125 minutes. Excess acetic anhydride was distilled in a Kugelrohr apparatus at temperatures up to 100° C. and at approximately 0.1 Torr pressure to obtain 26.8 g of an amber fluid. This sample was mixed with two smaller lots of material prepared in the same manner with acetic anhydride and also acetyl chloride as the acylating agents (since all lots had identical proton NMR spectra). Since this material was slightly cloudy, it was dissolved in hexane and passed through a 0.22 micron General Solvent membrane filter and then stripped to 32.31 g oil. Since NMR analysis indicated this material contained a trace of acetic anhydride it was again subjected to distillation on a Kugelrohr apparatus at 100° C. and approximately 0.1 Torr to obtain 32.01 g oil.

Example 9

This example illustrates the preparation of soybean oil monoisobutyrate according to FIG. 2. Hydrogenated epoxidized soybean oil (19.6 g, 0.0870 mole hydroxyl) was reacted with 209.9 g isobutyric anhydride (1.327 mole) and 12.0 mL pyridine equipped with magnetic stirring in a 250 mL flask an heated at 75-76° C. for 2.0 hours under an argon atmosphere. Excess isobutyric anhydride was removed by distillation in a Kugelrohr apparatus at temperatures up to 100° C. and pressures as low as 37 microns to obtain 13.61 g oil. IR spectral analysis of this material did not reveal anhydride or acid bands but since the sample did smell of isobutyric acid, this material was subjected to further hydrolysis by heating with 15 mL water and 15 mL pyridine at 65° C. for 2 hours with rapid stirring. This material was transferred to centrifuge tube with 150 mL ethyl acetate and 5 and rapidly shaken with 50 mL of aqueous wash solutions to obtain mixtures that were phase separated by centrifugation after which the lower phases were removed by pipette. The following solutions were used and the following wash pH values were observed: water (used as part of initial rinse), 10% sodium hydroxide (pH 10), 10% sodium hydroxide (pH 14), 10% hydrochloric acid plus extra 50 mL ethyl acetate (pH 0), 5% sodium bicarbonate (pH 8), 100 mL water and 50 mL ethyl acetate (pH 6.5), 100 mL water and 50 mL ethyl acetate (pH 5.5). The ethyl acetate solution was dried over sodium sulfate, filtered through cotton and stripped in a rotary evaporator under aspirator pressure with a bath temperature of 50° C. and then at 0.1 Torr for 3 hours with a vacuum pump to obtain an oil. NMR and IR spectral analysis indicated that residual epoxy and hydroxyl functionality and isobutyric anhydride were not present in this oil.

Example 9A

Soybean Oil Monoisobutyrate

This example illustrates the preparation of soybean oil monoisobutyrate according to FIG. 2. In a 2 L 3-necked round bottom flask equipped with magnetic stirring and a reflux condenser equipped with a gas inlet tube was added 112.06 g hydrogenated soybean oil (0.490 mole hydroxyl groups) and 57.43 g isobutyryl chloride (0.539 mole) and 692 ml diethyl ether. The stirred reaction mixture was flushed with argon and kept under an argon atmosphere using a bubbler and 44.78 g pyridine (0.566 mole) was slowly added via a syringe through a septum in the flask neck without heating the flask. This mixture was refluxed 10 hours and then placed in a refrigerator before the pyridine was filtered through a medium porosity glass frit. The filtrate was washed with 350 ml portions of 5% hydrochloric acid (pH 0), 3 portions of 5% sodium bicarbonate (pH 9 each), water (pH 8), water (pH 6), water (pH 5). The ether layer was passed through cotton for preliminary drying and then dried over sodium sulfate. This mixture was stripped in a rotary evaporator under aspirator pressure and then in a Kugelrohr apparatus for 2 hour at 100° C. and 0.04 Torr and then at 115° C. and 0.02 Torr for 0.5 hour to obtain 102.1 g liquid. This material was passed though basic alumina (75 g) in a pressure filter apparatus using argon gas to force the material through the alumina bed and the product was passed two more times through the same alumina bed to obtain 65.0 g material having an acid value of 0.091.

Example 10

This example illustrates the preparation of soybean oil monohexanoate according to FIG. 2. Hydrogenated epoxidized soybean oil (50.0 g, 0.218 mole hydroxyl), 33.71 g hexanoyl chloride (0.2505 mole) and 20.3 mL pyridine (0.2505 mole) were dissolved in 270 mL anhydrous ether and refluxed 7 hours under an argon atmosphere. After sitting overnight, the precipitate of pyridine hydrochloride was removed by filtration through a glass frit using ether rinses. This solution was transferred to a separatory funnel and extracted with washed with 150 mL of the following aqueous solutions to which had the following pH values after removal: 2×150 mL 5% hydrochloric acid (pH 0,0), 150 mL 10% sodium bicarbonate (pH 9), 150 mL 10% sodium bicarbonate (pH 9), and 150 mL 10% sodium bicarbonate (pH 9). At this point it was determined by evaporating a small portion of the ether solution and obtaining an IR spectrum that residual acid chloride was still present. Since continued extraction with sodium bicarbonate solution did not appreciably reduce the hexanoyl chloride concentration, the ether solution was dried and evaporated and this residue was heated with 15 mL water and 5 mL pyridine at 65° C. for 3 hours with rapid stirring. This material was transferred to a separatory funnel with 150 mL ethyl acetate and 150 mL water and rapidly shaken with 150 mL of aqueous wash solutions to obtain mixtures that were phase separated within the separatory funnel. The following wash solutions were used and the following wash pH values were observed: water, 10% sodium hydroxide (pH 9), 10% sodium hydroxide plus 75 mL ethyl acetate, 10% hydrochloric acid (pH 0), 5% sodium bicarbonate (pH 8), 100 mL water (pH 6), 100 mL water (pH 6). The ethyl acetate solution was dried over sodium sulfate, filtered through cotton and stripped in a rotary evaporator under aspirator pressure with a bath temperature of 50° C. and then with vacuum pump pressure for 2 hours to obtain 25.01 g of an oil. NMR and IR spectral analysis indicated that residual epoxy and hydroxyl functionality and hexanoyl chloride were not present in this oil.

Example 10A

Soybean Oil Monohexanoate

This example illustrates the preparation of soybean oil monohexanoate according to FIG. 2. The method described in Example 10 was used to prepare this material, except that 119.4 g of hydrogenated epoxidized soybean oil was used and the epoxidized soybean oil was reduced using ethanol rather than acetic acid as solvent, while maintaining all reagent ratios. After the pyridine/water procedure was used (described in Example 10) to hydrolyze and remove trace acid chloride, 119.1 g of liquid was obtained having an acid value was found to 0.54. This material was passed though basic alumina (75 g) in a pressure filter apparatus using argon gas to force the material through the alumina bed and the product was passed two more times through the same alumina bed to obtain 78.3 g liquid having an acid value of 0.144. The alumina bed was extracted with ether which was stripped to obtain an additional 19.8 g material having an acid value of 0.149.

Example 11

This example illustrates the preparation of soybean oil mono 2-ethylhexanoate according to FIG. 2. Hydrogenated epoxidized soybean oil (47.0 g, 0.206 mole hydroxyl), 37.54 g 2-ethylhexanoyl chloride (0.2262 mole) and 19.94 mL pyridine (0.2467 mole) were dissolved in 270 mL anhydrous ether and refluxed 10 hours under an argon atmosphere. After sitting overnight, the precipitate of pyridine hydrochloride was removed by filtration through a General Solvent membrane filter using ether rinses. This mixture developed solid so it was placed in a refrigerator overnight and refiltered though a General Solvent membrane filter. This was stripped under aspirator pressure to obtain 74.7 g of a cloudy white solution that was heated 37.5 mL water and 12.5 mL pyridine at 65° C. for approximately 3 hours. This solution was transferred to centrifuge tubes with 150 mL ethyl acetate and with washed with 150 mL of the following aqueous solutions which had the following pH values after phase separation: 10% sodium hydroxide (pH 9), 10% sodium hydroxide (pH 9), 10% hydrochloric acid (pH 0), 150 mL 5% sodium bicarbonate (pH 9), 150 mL 10% sodium bicarbonate and 40 mL ethyl acetate (pH 9), 150 mL 10% sodium bicarbonate plus 40 mL ethyl acetate (pH 7-8), water plus 50 mL ethyl acetate (pH 6). At this point it was determined by evaporating a small portion of the ether solution and obtaining an IR spectrum that residual acid chloride was still present. Thus, the ether solution was dried and evaporated and this residue was heated with 38 mL water and 17 mL pyridine at 65° C. for six hours with rapid stirring. This material was transferred to a centrifuge tubes with 250 mL ethyl acetate and 100 mL water and rapidly shaken with 100 mL aqueous wash solutions to obtain mixtures that were phase separated by centrifugation. The following wash solutions were used and the following wash pH values were observed: water, 10% sodium hydroxide (pH 10), 10% sodium hydroxide (pH 11), 10% hydrochloric acid (pH 0), 10% hydrochloric acid (pH 0), 10% sodium bicarbonate (pH 8), 100 mL water (pH 5.5). The ethyl acetate solution was dried over sodium sulfate, filtered through filter paper and stripped in a rotary evaporator under aspirator pressure with a bath temperature of 50° C. and then at 0.04 Torr with a vacuum pump for 2.5 hours to obtain 25.96 g of an oil. NMR and IR spectral analysis indicated that residual epoxy and hydroxyl functionality and 2-ethylhexanoyl chloride were not present in this oil.

Example 11A

Soybean Oil Mono(2-ethylhexanoate)

This example illustrates the preparation of soybean oil mono(2-ethylhexanoate) according to FIG. 2. The method described in Example 11 was used to prepare this material except that 116.2 g of hydrogenated epoxidized soybean oil was used and the epoxidized soybean oil was reduced using ethanol rather than acetic acid as solvent, while maintaining all reagent ratios. The pyridine/water procedure (described in Examples 3, 4, 5, 6, 6A, 7, 10, 10A, 12, 13, and 14) to hydrolyze and remove excess acid chloride was used after removal of pyridine hydrochloride to produce 155.8 g having an acid value of 0.68. The proton NMR spectrum of this material had absorptions at 4.76-5.04 ppm corresponding to the methine hydrogen atoms attached to ester groups. This material (150.0 g) was passed though basic alumina (71 g) in a pressure filter apparatus using argon gas to force the material through the alumina bed and the product was passed two more times through the same alumina bed to obtain 104.2 g liquid having an acid value of 0.16.

Example 12

Soybean Oil Mixed Mono(Hexanoate/Acetate, 50:50)

This example illustrates the preparation of soybean oil mixed mono(acetate/hexanoate, 50:50) according to FIG. 2. In a 1 L round bottom flask equipped with magnetic stirring and reflux condenser equipped with a gas inlet tube was charged 58.50 g hydrogenated soybean oil (prepared by reduction of epoxidized soybean oil in ethanol rather than acetic acid; 0.2559 mole hydroxyl groups), 23.08 g pyridine (0.2918 mole) and 337 ml diethyl ether. The stirred reaction mixture was kept under an argon atmosphere using a bubbler and 19.64 g hexanoyl chloride (0.1459 mole) and acetyl chloride (11.45 g; 0.1459 mole) were added sequentially via a syringe (while adding the hexanoyl chloride first) through a septum in the flask neck without heating the flask. The mixture was then refluxed 10 hours, and the mixture was cooled to refrigerator temperatures after which the pyridine hydrochloride was filtered using a 0.22 micron General Solvent (GS) membrane and the solvent was removed with a rotary evaporator. To hydrolyze the excess acid chlorides, 22.6 ml pyridine, 62.7 ml water were added to this mixture which was heated in an oil bath maintained at 65° C. while stirring vigorously with mechanical stirring for eight hours. This mixture was transferred to a 1 L plastic bottle with 187 ml ethyl acetate and the mixture was extracted with 50 ml portions of aqueous wash solutions after which the lower phases were removed by pipette and the following wash pH values were observed: 10% sodium hydroxide (pH 9), 10% sodium hydroxide (pH 9), 10% HCl (pH 0), 5% sodium bicarbonate (pH 9), 10% sodium bicarbonate plus 50 mL extra ethyl acetate (pH 9), 10% sodium bicarbonate plus 113 mL extra ethyl acetate (pH 9), water (pH 9), water (pH 7-8), water (pH 5-6). The mixture was dried over sodium sulfate overnight and the solvent was first stripped in a rotary evaporator using aspirator pressure at 70° C. to obtain 55.49 g of material that was further stripped in a Kugelrohr apparatus (with vacuum pump) for 4 hours at 120° C. at 0.08-0.02 Torr pressure to obtain 53.97 g clear, light yellow and moderately viscous liquid. This material had an acid value of 0.96.

Example 13

Soybean Oil Mixed Mono(Hexanoate/Isobutyrate, 50:50)

This example illustrates the preparation of soybean oil mixed mono(isobutyrate/hexanoate, 50:50) according to FIG. 2. In a 1 L round bottom flask equipped with a mechanical stirring apparatus and reflux condenser equipped with a gas inlet tube was charged 58.05 g hydrogenated soybean oil (prepared by reduction of epoxidized soybean oil in ethanol rather than acetic acid; 0.2559 mole hydroxyl groups), 23.08 g pyridine (0.2918 mole) and 337 ml diethyl ether. The stirred reaction mixture was kept under an argon atmosphere using a bubbler and isobutyryl chloride (13.50 g; 0.1459 mole) and 19.64 g hexanoyl chloride (0.1459 mole) were added sequentially via a syringe (while adding the isobutyryl chloride first) through a septum in the flask neck without heating the flask. The mixture was then refluxed 10 hours, after which the pyridine hydrochloride was filtered using a 0.22 micron General Solvent (GS) membrane and the solvent was stripped on a rotary evaporator. To hydrolyze the excess acid chlorides, 22.6 ml pyridine and 62.7 ml water were added to this mixture which was heated in an oil bath maintained at 65° C. while stirring vigorously with mechanical stirring for five hours. This mixture was transferred to a 1 L plastic bottle with 187 ml ethyl acetate and the mixture was extracted with 50 ml portions of aqueous wash solutions after which the lower phases were removed by pipette and the following wash pH values were observed: 10% sodium hydroxide (pH 9), 10% sodium hydroxide (pH 9), 10% HCl (pH 0), 5% sodium bicarbonate (pH 9), 10% sodium bicarbonate plus 50 mL extra ethyl acetate (pH 9), 10% sodium bicarbonate plus 113 mL extra ethyl acetate (pH 9), 94 mL water (pH 7). The mixture was dried over sodium sulfate overnight and the solvent was first stripped in a rotary evaporator using aspirator pressure at 70° C. and then further stripped in a Kugelrohr apparatus (with vacuum pump) for 2.5 hours at 120° C. at 0.07 Torr to obtain 70.05 g clear, almost colorless and moderately viscous liquid. The proton NMR spectrum of this material had absorptions at 4.80-5.04 ppm corresponding to the methine hydrogen atoms attached to ester groups. This material had an acid value of 0.86.

Example 14

Soybean Oil Mixed Mono(Hexanoate/2-Ethylhexanoate, 50:50)

This example illustrates the preparation of soybean oil mixed mono(hexanoate/2-ethylhexanoate, 50:50) according to FIG. 2. In a 1 L round bottom flask equipped with magnetic stirring and reflux condenser equipped with a gas inlet tube was charged 80.40 g hydrogenated soybean oil (prepared by reduction of epoxidized soybean oil in ethanol rather than acetic acid; 0.3519 mole hydroxyl groups), 31.56 g pyridine (0.3990 mole) and 462 ml diethyl ether. The stirred reaction mixture was kept under an argon atmosphere using a bubbler and 32.61 g 2-ethylhexanoyl chloride (0.1995 mole) and hexanoyl chloride (26.99 g; 0.1995 mole) were added sequentially via a syringe (while adding the 2-ethylhexanoyl chloride first) through a septum in the flask neck without heating the flask. The mixture was then refluxed 10 hours, and the mixture was cooled to refrigerator temperatures after which the pyridine hydrochloride was filtered using a 0.22 micron General Solvent (GS) membrane and the ether was removed in a rotary evaporator. To hydrolyze the excess acid chlorides, 21.2 ml pyridine and 64.1 ml water were added and the mixture which was heated in an oil bath maintained at 65° C. while stirring vigorously with mechanical stirring for eight hours. This mixture was transferred to a 1 L plastic bottle with 200 ml ethyl acetate and the mixture was extracted with 100 ml portions of aqueous wash solutions after which the lower phases were removed by pipette and the following wash pH values were observed: 10% sodium hydroxide (pH 10), 10% sodium hydroxide (pH 10), 10% sodium hydroxide plus 50 ml ethyl acetate (pH 10), 20% sodium hydroxide (pH 14), HCl (pH 1), 5% sodium bicarbonate (pH 9), 10% sodium bicarbonate plus 50 mL extra ethyl acetate (pH 9), 10% sodium bicarbonate plus 113 mL extra ethyl acetate (pH 9), water (pH 9), water (pH 7), water (pH 6.5-7.0), water (pH 5.5-6). The mixture was dried over sodium sulfate and the solvent was first stripped in a rotary evaporator using aspirator pressure at 40° C. and then further stripped in a Kugelrohr apparatus (with vacuum pump) for 2 hours at 140° C. at 0.03 Torr to obtain 70.0 g clear, light yellow and moderately viscous liquid. This material had an acid value of 0.64.

TABLE 1

Homosubstituted Soybean Oil Diesters Prepared by Reaction of ESO and Anhydrides by Heating with (1) TEA in Autoclave, or (2) $K_2CO_3$

| Lubricant | | | Rel. | Rel. | | | | Cld. Pt. ° C./ with P. Pt. | Pour | Pour Pt. c 1% Lub. |
|---|---|---|---|---|---|---|---|---|---|---|
| Diester | Example No. | Process | Moles Anhyd. | Moles Acid | AV | Wt. (g) | Clarity Color | Depr./ ° C. | Pt. ° C. | 7671 ° C. |
| Diacetate | 1 | 1 | | | | | | NA | 13 | — |
| Diacetate | 1A | 1 | | | | | | — | — | — |
| Diacetate | 1B | 1 | | | | | | −18 | −18 | — |
| Dipropionate | 3 | $K_2CO_3$ | 1.20 | — | — | 64.7 | clear | none | −7 | −7 |
| Dipropionate (mid oleic) | 3A | 4A** | 1.25 | 0.248 | 0.20 | | clear | | | |
| Diisobutyrate | 4 | $K_2CO_3$ | 1.20 | — | — | 56.1 | clear | none | −7 | −9 |
| Diisobutyrate | 4A | 4A** | 1.233 | 0.243 TEA = 0.08 | 0.34 | 54.9 | Clear, lt. orange | −12 | −11 | — |
| Diisobutyrate | 4B | 4A** | 1.31 | 0.247 TEA = 0.08 | 0.28 | 115.0 | Clear, dk. yellow | | | |
| Diisobutyrate (mid oleic) | 4C | 4A** | 1.25 | 0.249 | 0.24 | 70.6 | clear | −12/−24 | −12 | |
| Bis (2-ethylbutyrate) | 5 | $K_2CO_3$ | 1.20 | — | — | 37.9 | clear | none | −12 | −18 |
| Bis (2-ethylbutyrate) | 5A*** | $K_2CO_3$ | | — | 0.13 | 344 to 213 | clear | −12/nil | −12 | −12 |
| Dihexanoate | 6 | $K_2CO_3$ | 1.20 | — | — | 65.6 | clear | −12/ −24 | −12 | −18 |
| Dihexanoate | 6A*** | $K_2CO_3$ | | — | 0.06 | 179 | clear | −14/−12 | −21 | −23 |
| Dihexanoate | 6B | 4A** | 1.254 | 0.248 | 1.58 0.63 | 148.6 | clear | −13/−15 | −16 | −18 |
| Dihexanoate (mid oleic) | 6C | 4A** | 1.252 | 0.248 | 0.64 | 115.4 | clear | −12/−4 | −21 | −23 |
| Bis (2-ethylhexanoate) | 7 | $K_2CO_3$ | 1.20 | — | — | 41.0 | clear | none | −7 | −4 |
| Bis (2-ethylhexanoate) | 2 | 4A**** | 1.256 | 0.247 | 0.42 0.38 | 75.5 | sl. turbid | Na/ nil | −14 | −12 |
| Bis (2-ethylhexanoate) | 7A*** | $K_2CO_3$ | | — | 0.38 | 210.6 | clear | — | — | — |
| Bis (2-ethylhexanoate) (mid-oleic) | 7C** | 4A** | 1.252 | 0.248 | 0.25 | | | none | 0/ | |
| Control 1 RBD Soybean Oil | | | | | | | | −2 | −9 | — |
| Control 2 RBD Soybean Oil | | | | | | | | −3 | −9 | — |
| Control 3 High Oleic (82%) Soybean Oil | | | | | | | | — | −15 | — |

| Lubricant | | Vis@ | | Penn. State Micro-Oxidation | | | | | |
|---|---|---|---|---|---|---|---|---|---|
| | Example | 40° C./ | | Deposit Wt. % | | | Evaporative Wt. % | | |
| Diester | No. | 100° C. | V.I. | 30 min | 60 min | 90 min | 30 min | 60 min | 90 min |
| Diacetate | 1 | 3750/99 | 85 | 0.90 | | | 5.2 | | |
| Diacetate | 1A | — | — | 1.1 | | | 3.6 | | |

TABLE 1-continued

Homosubstituted Soybean Oil Diesters Prepared by Reaction of ESO and Anhydrides by Heating with (1) TEA in Autoclave, or (2) $K_2CO_3$

| | | | | | | | | | |
|---|---|---|---|---|---|---|---|---|---|
| Diacetate | 1B | 4800/120 | 90 | 1.6 | | | 4.1 | | |
| Dipropionate | 3 | 1242/ 53.8 | 89 | 0.67 | — | — | 6.71 | — | — |
| Dipropionate (mid oleic) | 3A | 638/ 44.8 | 117 | | 1.92 | | | 7.69 | |
| Diisobutyrate | 4 | 1380/ 60.3 | 94 | 2.12 | — | — | 6.10 | — | — |
| Diisobutyrate | 4A | 1050/ 51.6 | 96 | 0.73 | — | — | 4.88 | — | — |
| Diisobutyrate | 4B | 1090/ 53.2 | 96 | | 2.40 | | | 8.7 | |
| Diisobutyrate (mid oleic) | 4C | 607/ 41.0 | 110 | | 3.27 | | | 11.5 | |
| Bis (2-ethylbutyrate) | 5 | 1200/ 68.7 | 119 | 0.75 | — | — | 2.76 | — | — |
| Bis (2-ethylbutyrate) | 5A*** | 1170/ 60.4 | 104 | 0.49 | 3.52 | 7.96 0.00* | 2.92 | 4.27 | 7.21 4.46* |
| Dihexanoate | 6 | 385/ 36.8 | 141 | 2.95 | — | — | 3.93 | — | — |
| Dihexanoate | 6A*** | 463/ 38.8 | 129 | 0.98 1.78 | 2.67 | 7.26 0.74* | 2.46 7.44 | 6.07 | 9.93 2.54* |
| Dihexanoate | 6B | 457/ 32.4 | 103 | 0.74 | to test | to test | 6.93 | to test | to test |
| Dihexanoate (mid oleic) | 6C | 349/ 33.6 | 137 | 1.98 | 2.95 | 13.7 0.51* | 4.94 | 8.60 | 10.38 1.27* |
| Bis (2-ethylhexanoate) | 7 | 766/ 55.5 | 131 | 1.00 | — | — | 5.72 | — | — |
| Bis (2-ethylhexanoate) | 2 | 715/ 47.0 | 114 | 2.48 | — | — | 5.71 | — | — |
| Bis (2-ethylhexanoate) | 7A*** | — | — | — | — | — | — | — | — |
| Bis (2-ethylhexanoate) (mid-oleic) | 7C** | 518/ 41.3 | 126 | | 5.50 | | 3.65 | | |
| Control 1 RBD Soybean Oil | | 32/7.7 | 227 | 9.2 | | | 7.4 | | |
| Control 2 RBD Soybean Oil | | 32/7.8 | 229 | 4.5 | | | 21.8 | | |
| Control 3 High Oleic (82%) Soybean Oil | | 40/9.0 | 218 | 3.5 | | | 16.3 | | |

*= 1% ZDDP (LZ 1395)

**The process according to Example 4A is used for preparation.

***The process according to Example 5, and 6 is used, except steam deodorization is used in examples 5A, 6A and 7A.

****The process according to Example 4A plus hot water extraction and addition of ethanol amine to react with excess anhydride.

Example 1A is a repeat test of Example 1 material, and 1B is a repeat preparation of Example 1.

TABLE 2

Homosubstituted and Heterosubstituted Soybean Oil Monoesters Prepared by Acylation of Hydrogenated ESO

| Lubricant | | | | | | | | | | | | Penn. State Micro-Oxidation (180° C.) | | | | | |
|---|---|---|---|---|---|---|---|---|---|---|---|---|---|---|---|---|---|
| | | | | | | | | | | | | Deposit Wt. % | | | Evaporative Wt. % | | |
| Monoester | Example No. | Process | Rel. Moles Anhyd1/ Anhyd2 | AV | Wt. (g) | Clarity | Cld. Pt. ° C. | Pour Pt. ° C. | Pour Pt. c 1% Lub. 7671 ° C. | Vis@ 40° C./ 100° C. | V.I. | 30 min | 60 min | 90 min | 30 min | 60 min | 90 min |
| Homosubstituted Soybean Oil Monoesters | | | | | | | | | | | | | | | | | |
| Acetate | 8 | $Ac_2O$/Py | — | — | | clear | −1 | −4 | — | 360/28 | 104 | 0.48 | — | — | 6.22 | — | — |
| Isobutyrate | 9 | Isobut. Anhy/Py | — | — | | clear | −6 | −7 | −12 | 120/30 | 281 | 3.02 | — | — | 4.53 | — | — |
| Isobutyrate | 9A | Isobut. Anhy/Py | — | 0.09 | 65 | clear | — | — | — | — | — | 2.15 | — | — | 3.85 | — | — |
| Hexanoate | 10 | Hex. Cl/ Py | — | — | 25 | clear | −4 | −15 | −18 | 210/25 | 151 | 2.23 | — | — | 4.72 | — | — |
| Hexanoate | 10A | Hex. Cl/ Py | — | 0.14 | 78 | clear | — | — | — | — | — | 3.23 | — | — | 8.11 | — | — |
| 2-Ethyl-hexanoate | 11 | 2-Et.hex. Cl/Py | — | | 26 | clear | −12 | −18 | −12 | 740/28 | 36 | 2.27 | — | — | 7.65 | — | — |

TABLE 2-continued

Homosubstituted and Heterosubstituted Soybean Oil Monoesters Prepared by Acylation of Hydrogenated ESO

| Lubricant | | | | | | | | | Pour Pt. c | | | Penn. State Micro-Oxidation (180° C.) | | | | | |
|---|---|---|---|---|---|---|---|---|---|---|---|---|---|---|---|---|---|
| | | | | | | | | | | | | Deposit Wt. % | | | Evaporative Wt. % | | |
| Monoester | Example No. | Process | Rel. Moles Anhyd1/ Anhyd2 | AV | Wt. (g) | Clarity | Cld. Pt. ° C. | Pour Pt. ° C. | 1% Lub. 7671 ° C. | Vis@ 40° C./ 100° C. | V.I. | 30 min | 60 min | 90 min | 30 min | 60 min | 90 min |
| 2-Ethyl-hexanoate | 11A | 2-Et.hex. Cl/Py | — | Init. 0.68 0.16 | 104 | clear | — | — | — | — | — | 2.93 | — | — | 4.97 | — | — |
| Heterosubstituted Soybean Oil Monoesters | | | | | | | | | | | | | | | | | |
| Hexanoic, Acetic | 12 | Acid chlorides | 0.57/ 0.57 | 0.96 | 54 | clear | −12 | −12 | — | 260/25 | 126 | 1.23 | — | — | 3.46 | — | — |
| Hexanoic, Isobutyric | 13 | Acid chlorides | 0.57/ 0.57 | 0.86 | 70 | clear | −13 | −24 | −21 | 210/23 | 133 | 1.75 | 2.98 | 4.24 0.52* | 4.51 | 6.70 | 10.97 0.26* |
| Hexanoic, 2-Ethylhex. | 14 | Acid chlorides | 0.57/ 0.57 | 0.64 | 70 | clear | −14 | −22 | −23 | 230/24 | 135 | 0.77 | 3.13 | 5.54 0.53* | 6.39 | 3.39 | 7.31 0.00* |

*= 1% ZDDP (LZ 1395)

ESO—epoxidized soybean oil

Lubrication screening tests were performed as described in Tables 1, 2 and 3 for soybean oil diesters and monoesters.

The Penn. State micro-oxidation test involves heating samples on a stainless steel surface while being exposed to air and measuring the deposit weight percent and evaporation weight percent. Decreased percentages compared to standard materials provide a measure of the oxidative stability of lubricant candidates. All oxidative stability tests were performed without addition of oxidative stabilizers. It can be seen in Tables 1, 2 and 3 that oils of the present invention generally gave much lower deposit and evaporation percentages than RBD soybean oil as well as high oleic soybean seed oil. Increased oxidative stability should be afforded to the modified oils of the present invention compared to non-modified RBD soybean oil by addition of the same quantities of antioxidants to provide increased supplementary oxidative stability. This effect was demonstrated by adding the antioxidant zinc dialkyldithiophosphate (2DDP) at 1% level. Significantly, soybean oil diester samples 4A, 5 and especially 5A which had been purified by steam distillation and 7 gave very low deposit weight percents that are attributed to the use of ester groups that are branched with alkyl groups at positions alpha to the ester carbonyl group providing additional oxidative stability to the fatty acid backbone. Even though hydrolytic stability was not evaluated in these samples, it is expected that these ester groups having branching at the position alpha to the carbonyl groups will possess substantially increased hydrolytic stability compared to ester side chains not having this branching. Example 5 also provides among the lowest evaporative weight loss percent of all prepared samples. Examples 1, 3, 4A, 6B, 8 12, 13 and 14 also provided low deposit weight percents. It can also be seen that 1% ZDDP also significantly improved the deposit weight % as seen in samples 5A, 6A, (purified by steam deodorization) and example 6B. It is also believed that evaporation of low quantities of residual solvent is partially contributing to evaporative weight loss percents.

Notable low evaporation weight percents were obtained with examples 1A, 1B, 5, 5A, 6, 6A, 12, 13 and 14. I can also be seen that 1% ZDDP significantly improved the evaporative weight % as seen in samples 5A, 6C, 13 and 14.

It can be seen that the viscosities of soybean oil diesters and monoesters at both 40° C. and 100° C. are significantly higher than the viscosities of triglyceride controls and the viscosity of any diester is higher than the viscosity of the corresponding monoester when the same sized R or R' groups are compared. All oils tested have been shown to be biodegradable and are expected to find use as lubricant base oils and viscosity enhancers due to their high viscosities. Soybean oil diacetates (samples 1, 1A, and 1B) provide particularly large viscosity improvements and may have special application as a rock drilling fluid since high viscosity oils are needed for this application. Being biodegradable and non-toxic would be an especially valuable attribute for this application since such drilling fluids are left in the rock strata and water tables traversed during well drilling.

The viscosity index is a measure of the change in viscosity with changes in temperature, with materials having a desirable smaller change in viscosity as the temperature is changed over a certain temperature interval having a larger viscosity index. Oils of the present invention have a range of viscosity indices, one of which, sample 9 (soybean oil monoisobutyrate) has a viscosity index that is significantly higher than soybean oil controls.

The cloud points for all samples measured were much better than the controls. The cloud point is an indication of internal phase separation typically of saturated components and is preferably low. The designation "None" in Table 1 indicates that no cloud points were observed to the lowest temperature involved in pour point determinations. The measured cloud points for all soybean oil diester samples showed a marked improvement over soybean oil controls. For soybean oil monoesters, the cloud points for all samples other than 8 and 11 were better than that of the control RBD Soybean Oil, with samples 12, 12 and 14 being much better than soybean oil.

The pour point of a lubricant represents the lowest temperature at which a material will pour according to ASTM D97 and should be as low as possible to allow low temperature applications. Small amounts of pour point depressants can also provide advantageous decreases in pour points. Pour points were measured and are listed in Tables 1 and 2. Soybean oil diester samples 5, 5A, 6, 6A and 6B provided improvements in pour point over soybean oil controls. Significantly, for soybean oil diesters, the best results were obtained for linear and branched six carbon ester side chains (examples 5, 5A, 6, 6A, 6B, and 6C). The best behavior was attained with soybean oil dihexanoate that had been steam deodorized (6A) or was derived from midoleic soybean oil (6C). Pour points for a mixture of the material of the invention with 1% Lubrizol 7671A are shown in Tables 1, 2, and 3. Pour points using 1% Lubrizol 3715 were also tested for example 6 and gave similar results. Significantly reduced pour points with the Lubrizol materials were obtained for samples 5, 6, and 6C. It is noteworthy that pour points of −21° C. were attained with soybean oil dihexanoate that had been deodorized (sample 6A) and also derived from mid-oleic soybean oil (example 6C). Also both of these samples had pour points of −23° C. when 1% pour point depressant was added. These low pour points provide distinct advantages over soybean oil.

Pour points were also evaluated for homosubstituted soybean oil monoesters and it was found that the hexanoate (example 10) and 2-ethylhaxanoate (example 11) had pour points of −15° C. and −18° C., respectively. It was also determined that the heterosubstituted monoesters having about 1:1 ratios of hexanoate and isobutyrate (example 13) and of hexanoate and 2-ethylhexanoate (sample 14) had pour points of −24° C. and −22° C., respectively.

Broadly the results are summarized as follows: It was found that micro-oxidation properties were comparable to those of mineral base and synthetic oils. High viscosities were attained in a number of samples, thus facilitating their use as biobased oils, additives, and viscosity enhancers. Viscosity indices in general peaked and then decreased as size of R was increased. Peak viscosity indices were noted as follows: Diesters (Dihexanoate—141, sample 6); Monoesters (Monoisobutyrate—281). Pour points in general minimized as R was increased, for example: Diesters (Dihexanoate—-12° C., -21° C., and -23° C. with pour point depressants, example 6A); Monoesters (Monoisobutyrate, -7° C., and −12° C. with a pour point depressant, sample 9; Monohexanoate, −15° C., and −18° C. with a pour point depressant, sample 10 and mono 2-ethylhexanoate, −18° C.).

Four Ball Wear Test: One important property of a lubricant is that it minimize wear between two surfaces making contact and moving past each. One method to measure the ability of a lubricant to minimize wear is to measure the wear scars obtained in 4-ball wear tests as described in ASTM method D4172. The 4-ball wear test provides non-conformal and point contact between surfaces and is a very aggressive measure of the wear-mediating properties of lubricants. Tested as controls were RBD soybean oil, Mobil SHC-634 gear oil and an SAE 10W-30 motor oil along with modified oils of the present invention. It can be seen under 18 kg load conditions that a number of candidates of the present invention gave significantly smaller wear scar diameters than soybean oil and one material, soybean oil dihexanoate with no additives, gave a wear scar diameter that was essentially the same as the two commercial lubricants that contain anti-wear components. When the well-known anti-wear and anti-oxidative material zinc dialkyldithiophosphate (ZDDP) was used at 1 percent levels under 18 kg load, wear scar diameter of materials of the present invention were similar or better than those from soybean oil and several approached the wear scar diameters of the two commercial lubricants. Under 40 kg load conditions, all materials of the present invention had larger wear scars compared to that from soybean oil. However, when 1 percent ZDDP was added, a number of lubricants of the present invention had wear scar diameters that were smaller than that of that from soybean oil and approached the wear scar diameters of the commercial lubricants. These test results indicate that attaching ester groups along the fatty acid groups of triglycerides as found in certain soybean oil monoesters and diesters can, depending on the applied contact force, lead to lower wear than found in non-modified vegetable oils and specifically soybean oil, either when containing or not containing the additive ZDDP in low concentrations.

Seal Material Compatibility Test: Lubricants are typically encased in compartments that have seals between non-moving and moving parts. A desirable seal property is that it undergoes minimal swelling and maintains its original hardness when exposed to warm or hot lubricant. Accordingly, tests were performed to determine the degree of swelling and change in hardness of two elastomers when exposed to lubricants of the present invention and soybean oil at 68° C. for 24 hours. The elastomers tested were ethylene propylene diene (EPDM) and nitrile rubber. When EPDM was tested, it can be seen that all four lubricants of the present invention induced significantly less swelling, based on dimensional and volume changes, and also maintained the original hardness much better than soybean oil. When nitrile rubber was tested, there was very little difference between the lubricants of the present invention and soybean oil in dimensional stability as well as hardness of this rubber. These test results indicate, depending on the specific seal material being used, that the lubricants of the present invention can provide significantly enhanced dimensional stability and also maintain the inherent hardness of individual elastomers in comparison to these same properties afforded by non-modified vegetable oils and specifically soybean oil.

Another embodiment of the invention provides heterosubstituted diesters and monoesters. Typical structures for the heterosubstituted diesters and monoesters are illustrated immediately below.

Formula A

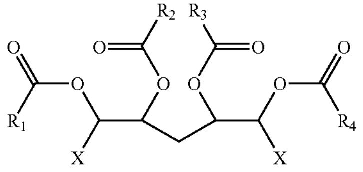

Homo- and Heterosubstituted Diesters

Formula B

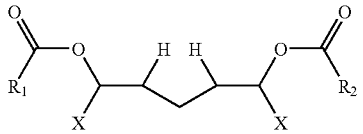

Homo and Heterosubstituted Monoesters

Formula A represents one group of diesters from fatty acid groups (e.g. from linoleic acid) where R1, R2, R3, and R4 can be the same or different sized groups having from 1-18 carbons. X represents the rest of the fatty acid within a triglyceride.

Formula B represents one group of monoesters from fatty acid groups (e.g. from linoleic acid) where R1 and R2 can be the same or different groups having from 1-18 carbons. X represents the rest of the fatty acid within a triglyceride. In formula B, other regioisomers are allowed whereby the vicinal hydrogenation (H) and ester groups ($-0_2CR$) are exchanged.

In the above formulas other regioisomers are allowed. Any number of acylating agents can be used (e.g. acid anhydrides or acid chlorides as appropriate). The above structures specify a maximum of only four different groups in the diester derived from linoleate and two different groups in the monoester derived from linoleate. It is important to note that it is possible to use a mixture of as many different acylating reagents as desired in either the diester or monoester cases that would populate the two different structures shown above in a manner proportional to their relative concentrations and their relative reactivities. This applies to each fatty acid arm of the triglyceride.

By placing different sized R groups within the same fatty acid backbone within triglycerides, it is expected that the resulting soybean oil, or vegetable oil in general, diesters and monoesters will have reduced pour points, increased responses to pour point depressants, and advantageous variations in viscosities.

Mixed diesters may be obtained by reacting epoxidized soybean oil or epoxidized oils in general, with mixtures of anhydrides having the structures $(R_nCO)_2O$ and $(R_mCO)_2O$ and a tertiary amine and optionally catalyzing with (a) either $R_1CO_2H$ or $R_2CO_2H$ where the acids can be the same or different from the anhydride(s) and a tertiary amine, or water and a tertiary amine or (b) potassium or other metal carbonate.

Mixed monoesters may be obtained by reacting hydrogenated epoxidized soybean oil, or hydrogenated epoxidized vegetable oils in general, with mixtures of anhydrides having structures $(R_1CO)_2O$ and $(R_2CO)_2O$ where the anhydrides may be the same or different or mixtures of acid chlorides having structures $R_1COCl$ and $R_2COCl$ where the acid chlorides may be the same or different. Tertiary amines or aromatic amines (e.g. such as pyridine) may be used as catalysts.

Heterosubstituted diesters and monoesters have been made according to the immediately above described methods scheme and the details outlined in Table 3 immediately below.

TABLE 3

Heterosubstituted Soybean Oil Diesters Prepared By Reaction of ESO and Anhydrides By Heating With TEA in Autoclave or with $K_2CO_3$

| Lubricant Diester | Example No. | Process | Rel. Moles Anhyd1/Anhyd2 | Rel. Moles Acid* | AV | Wt. (g) | Clarity | Cld. Pt. ° C. | Pour Pt. ° C. | Pour Pt. c 1% Lub. 7671 ° C. |
|---|---|---|---|---|---|---|---|---|---|---|
| Hexanoic, Acetic* | 3-1 | Example 2** | 0.500/ 0.755 | 0.248 | 0.29 | 122 | clear | Na | −7 | — |
| Hexanoic, Acetic* | 3-2 | Example 2 | 0.755/ 0.524 | 0.247 | — | 126 | turbid | Na | −7 | — |
| Hexanoic*, Propionic | 3-3 | Example 2 | 0.368/ 1.023 | 0.368 | 0.56 | 50 | clear | −9 | −12 | — |
| Hexanoic*, Propionic | 3-4 | Example 2 | 0.754/ 0.501 | 0.247 | — | 138 | clear | −12 | −12 | −12 |
| Hexanoic*, Propionic (mid-oleic) | 3-5 | Example 2 | 0.75/ 0.50 | 0.248 | | | | | −15 | |
| Hexanoic*, Propionic | 3-6*** | Example 3-$7_3$ | 0.720/ 0.480 | 0.060 | | 59.1 | clear | | | |
| Hexanoic, Isobutyric* | 3-7 | Example 2 | 0.754/ 0.500 | 0.246 | 0.20 | 120 | clear | −12 | −12 | — |
| Hexanoic, Isobutyric* | 3-8 | Example 2 | 0.368/ 1.023 | 0.378 | 0.30 | 132 | clear | −12 | −9 | — |
| Hexanoic, Isobutyric* | 3-9*** | Example 3-$7_3$ | 0.484/ 0.726 | 0.061? | 0.46 | 30 | clear | −12 | −12 | — |
| 2-Ethylhex.*, Propionic | 3-10 | Example 2 | 0.368/ 1.023 | 0.378 | 0.38 | | | −11 | −9 | — |
| 2-Ethylhex.*, Isobutyric | 3-11 | Example 2 | 0.368/ 1.023 | 0.378 | — | 140 | slight turbid | −10 | −9 | — |

| Lubricant Diester | Example No. | Vis@ 40° C./100° C. | V.I. | Penn. State Micro-Oxidation (180° C.) Deposit Wt. % 30 min | Deposit Wt. % 60 min | Deposit Wt. % 90 min | Evaporative Wt. % 30 min | Evaporative Wt. % 60 min | Evaporative Wt. % 90 min |
|---|---|---|---|---|---|---|---|---|---|
| Hexanoic, Acetic* | 3-1 | 1400/ 58 | 89 | 1.21 | — | — | 3.37 | — | — |
| Hexanoic, Acetic* | 3-2 | 1080/ 53 | 96 | 0.72 | — | — | 3.13 | — | — |
| Hexanoic*, Propionic | 3-3 | 735/ 42.2 | 98 | 0.73 | — | — | 4.37 | — | — |
| Hexanoic*, Propionic | 3-4 | 619/ 42.6 | 113 | 0.00 | — | — | 7.18 | — | — |
| Hexanoic*, Propionic (mid-oleic) | 3-5 | 406/ 36.4 | | | 3.28 | | | 5.30 | |
| Hexanoic*, Propionic | 3-6*** | | | | | | | | |
| Hexanoic, Isobutyric* | 3-7 | 585/ 41.7 | 116 | 1.73 | — | — | 6.40 | — | — |
| Hexanoic, | 3-8 | 756/ | 105 | 1.21 | — | — | 6.28 | — | — |

TABLE 3-continued

Heterosubstituted Soybean Oil Diesters Prepared By Reaction of ESO and Anhydrides By Heating With TEA in Autoclave or with $K_2CO_3$

| | | | | | | | | | |
|---|---|---|---|---|---|---|---|---|---|
| Isobutyric* | | 45.9 | | | | | | | |
| Hexanoic, | 3-9*** | 729/ | 110 | 0.47 | — | — | 5.44 | — | — |
| Isobutyric* | | 46.3 | | | | | | | |
| 2-Ethylhex.*, | 3-10 | 896/ | 96 | 1.19 | — | — | 5.25 | — | — |
| Propionic | | 47.2 | | | | | | | |
| 2-Ethylhex.*, | 3-11 | 818/ | 108 | 0.96 | — | — | 6.70 | — | — |
| Isobutyric | | 49.3 | | | | | | | |

*this identifies the carboxylic acid used in the reaction. The relative moles of acid used in preparing the mixed diester influences the final viscosity obtained. For example, in example 3-1, 1 mole of epoxy groups react with 0.500 mole of hexanoic anhydride, 7.55 mole acetic anhydride and 0.248 mole of acetic acid.

**preparation according to the procedure of example 2.

***preparation or examples 3-6 and 3-9 can be done by procedure according to examples 3-7 except that after the $K_2CO_3$ removal phase with a water wash, the excess anhydrates were removed entirely by using a Kugelrohr operated at about 140° C. at a pressure of about 0.03 Torr. For either of the exemplary processes (example 2 or examples 3-7), the product is treated in a Kugelrohr until the desired acid value is obtained.

Typical additives known in the art that have the potential to improve the overall performance of the materials according to the invention include the use of antiwear additives, pour point depressants, foam modifiers, detergents, antioxidants, and the like.

Furthermore, mixtures of any of the materials according to the present invention are expected to provide beneficial effects for specific uses.

Another type of lubricant candidate containing both diester and monoester functionality would be prepared by using a combination of approaches used to individually prepare vegetable oil or fat diesters and monoesters. This process would be performed by partial hydrogenation of epoxidized oil or fat and reacting derived mixture of epoxide and alcohol functionality with acid anhydrides in the presence of the same catalysts used to prepare diesters and monoesters separately. In this manner, diester and monoester functionality would both be introduced into fatty acids in the same or different triglycerides.

A significant issue concerning vegetable oil and fats are their high cloud points and pour points due mainly to the presence of relatively high levels of saturated fatty acids that have increased tendencies to crystallize at reduced temperatures. A method to overcome this deficiency is to interesterify the vegetable oil or fat with an oil or fat having an increased amount of unsaturation in their fatty acids as evidenced by their relatively high iodine numbers. Interesterification is a chemical process by which all fatty acids are randomly exchanged, so use of materials having high iodine numbers such as linseed or menhaden oil will result in materials with lower percent saturated fatty acids, thereby reducing their cloud points and pour points.

Soybean oils containing increased amounts of oleic acid and decreased amounts of linoleic acid are referred to as mid-oleic or high-oleic soybean oil, depending on the relative oleic acid contents. Triglycerides containing increased amounts of oleic acid have increased oxidative stability due to the decrease in doubly allylic methylene groups as found in linoleic and linolenic fatty acids. Thus, it is expected that preparing diester and monoester derivatives of mid-oleic and high-oleic soybean oil, or vegetable oils in general, will result in an enhanced oxidative stability compared to those demonstrated in diester and monoester derivatives of normal soybean oil. The same effects are expected when using other vegetable oils having increased oleic acid contents.

Vegetable oil and fat-based lubricants containing hydroxyl groups along the triglyceride fatty acid arms are accessible from diester and monoester lubricants described herein or by other means of adding hydroxyl groups directly to the double bonds of vegetable oils and fats. These derived polyhydroxy triglycerides are expected to be useful lubricants.

Example 4-1

Procedure to Prepare Soybean Oil Dihexanoate

The following example illustrates the preparation of soybean oil diesters using Reaction B of FIG. 1 whereby the reaction temperature is rapidly raised to 180° C. before the catalyst potassium carbonate was added. The advantage of this procedure over the procedures in Examples 3-7 is that the overall reaction time is shorter and can be run more reproducibly since when potassium carbonate is originally charged in the reaction flask, the reaction temperature must be raised slowly until an exotherm temperature is attained so that the reaction is maintained under control. Epoxidized soybean oil (200 g, 0.875 mole oxirane) and 225.17 g hexanoic anhydride (1.05 mole) were weighed into a 2 L 3-neck Round bottomed flask equipped with an argon gas inlet adapter, condenser, thermocouple, and mechanical stirrer. Powdered potassium carbonate (12.25 g, 0.089 mole) was weighed in an argon-filled glove bag and added to the flask that had been flushed with argon. A J-Kem heat controller was used to heat mixture to 180 C using a heating mantle and the potassium carbonate was added slowly with stirring at that temperature. The temperature spiked to 201 C before slowly relaxing back to 180 C over 1 hour and 40 minutes. Reaction was monitored by NMR and was complete after 3.5 hours total reaction time. After cooling, the reaction product was partitioned between 200 ml water and 200 ml diethyl ether that was then extracted with 200 ml portions of 10% sodium hydroxide, 10% hydrochloric acid, 10% sodium bicarbonate, and then washed with water to bring the aqueous pH to neutral. The ether solution was dried with magnesium sulfate, filtered through a medium frit filter, and then stripped on a rotary evaporator to with an aspirator and vacuum pump for 2 hours at 1.5 Torr and 60 C to obtain 383.0 g of clear/yellow oil.

Example 4-2

Procedure to Prepare Soybean Oil Dihexanoate

The following example illustrates the preparation of soybean oil diesters using Reaction B of FIG. 1 whereby the reaction temperature is rapidly raised to 180° C. before the catalyst potassium carbonate and the carboxylic acid corresponding to the acid anhydride is also added as a secondary catalyst. The advantages of this procedure over the procedures in Examples 3-7 include not only the advantages of the previous example but the secondary catalyst also provides shorter reaction times. Epoxidized soybean oil (200 g, 0.875 mole oxirane) and 225.45 g hexanoic anhydride (1.05 mole) and 5.29 g hexanoic acid (0.045 mole) were weighed into a 2 L 3-neck round bottomed flask equipped with an argon gas inlet adapter, condenser, thermocouple, and mechanical stirrer. A 3-Kem heat controller was used to heat the mixture to 180 C using a heating mantle and anhydrous potassium carbonate (12.42 g; weighed in a glove bag with argon) was added slowly with stirring at that temperature. The temperature spiked immediately to 229° C. even though the heating mantle was immediately removed and slowly returned to 180° C. over one hour. The reaction was monitored by NMR and was complete after 2 hours total reaction time. After cooling, the reaction product was partitioned between 200 ml water and 200 ml diethyl ether that was then extracted with 200 ml portions of 10% sodium hydroxide, 10% hydrochloric acid, 10% sodium bicarbonate, and then washed with water to bring the aqueous pH to neutral. The ether solution was dried with sodium sulfate, filtered through a medium frit filter, and then stripped on a rotary evaporator to with an aspirator for 2 hours at 60 C to obtain 368.8 g of clear/yellow oil.

Biodegradation

Test Samples: Samples: Example 14, Example 6A, Example BPAD

Sewage sludge for this test was obtained from the wastewater treatment plant in Hiram Ohio. Two weeks prior to officially starting the test, sludge microorganisms were pre-exposed to the test samples in order to enhance results as part of an optional inoculum pre-adaptation technique listed in ASTM 5864 Sec 8.3.1.

The carbon content of the canola oil control and the other formulations were determined according to procedure set forth in ASTM D-5291-02 for later calculation of biodegradability.

| Sample | Carbon Content (%) | Avg. % Biodegrability* |
|---|---|---|
| Canola oil (Control) | 77 | 76 |
| Example 14 | 73 | 71 |
| Example 6A | 70 | 68 |
| Example BPAD** | 65 | 74 |

*Biodegrability after 28 days

**A hexapropionate, acetate diester prepared according to the invention

Micro-Oxidation

The micro-oxidation test was used to evaluate the stability of the base oils. The test was run at 180° C. for 30 minutes and 60 minutes. Overall, the test showed excellent oxidation stability improvement in the oils modified according to the invention compared to the conventional and high oleic vegetable base oils. The oils also showed excellent response to zinc alkyldithiophosphate as shown in the micro-oxidation and the Four Ball Wear Test.

Viscosities

The viscosities were run to determine three important physical properties of the oils, Viscosity at 40° C., Viscosity at 100° C., and Viscosity Index.

Pour Point & Cloud Point

Pour points as low as −25° C. have been met without pour point depressants (PPD).

Below is a comparison of two oils according to the invention compared to a petroleum based stock (Petr. BS).

| | 50247-69-10 | 50247-85-16 | Petr. BS |
|---|---|---|---|
| Biobased | yes | yes | no |
| Viscosity @ 40° C. | 463 | 1170 | 448 |
| Viscosity @ 100° C. | 38.83 | 60.3 | 30 |
| Viscosity Index | 129 | 104 | 96 |
| Pour Point ° C. | −20.5 w/PPD | −12 | −12 |

The oils according to the invention can also be used as a lubricity additive, industrial thickener, and viscosity index improver.

While the forms of the invention herein disclosed constitute presently preferred embodiments, many others are possible. It is not intended herein to mention all of the possible equivalent forms or ramifications of the invention. It is to be understood that the terms used herein are merely descriptive, rather than limiting, and that various changes may be made without departing from the spirit of the scope of the invention.

We claim:

1. A method for making a modified triglyceride diester comprising a. providing an epoxidized triglyceride;

b. reacting the epoxidized triglyceride with an acid anhydride in the presence of a basic catalyst to produce a diester; and c. separating the diester from the catalyst and unreacted anhydride.

2. The method according to claim 1, wherein two or more different anhydrides are reacted.

3. The method according to claim 1, wherein the basic catalyst is a metal carbonate, bicarbonate, hydroxide, or carboxylate.

4. The method according to claim 1, wherein the basic catalyst is selected from the group consisting of $K_2CO_3$, $Na_2CO_3$, $KHCO_3$, and $NaHCO_3$.

5. The method according to claim 1, wherein the basic catalyst is separated with water partitioning and excess anhydride is hydrolyzed to its corresponding carboxylic acid.

6. The method according to claim 5, wherein the excess anhydride is hydrolyzed by steam to the corresponding carboxylic acid and removed by deodorization.

7. The method according to claim 1, wherein providing the epoxidized triglyceride comprises:

providing an animal oil, animal fat, plant oil, or plant fat having an iodine number above about 7; and epoxidizing said oil or fat.

8. The method according to claim 1 wherein the acid anhydride comprises a carboxylic acid anhydride having between one and about 18 carbon atoms.

9. The method according to claim 1, wherein epoxidizing said oil or fat takes place in the presence of a cosolvent.

10. The method according to claim 1, wherein the basic catalyst comprises a tertiary amine.

11. The method according to claim 10, wherein the tertiary amine comprises triethylamine.

12. The method according to claim 1, further comprising controlling the amount of anhydride in the reaction to provide interchain linkages.

13. The method according to claim 1, wherein two or more anhydrides are reacted to produce the diester and wherein the diester is a heterosubstituted diester.

14. The method according to claim 1 wherein the diester is a modified triglyceride heterosubstituted diester wherein adjacent carbon atoms originally joined by a double bond each have a pendant ester group and each of the ester groups is randomly selected from two or more different ester groups.

15. The method according to claim 14 wherein at least one small ester group comprising from 2 to 17 carbon atoms is selected and at least one large ester group comprising from 3 to 18 carbon atoms is selected, and the ester groups differ by at least one carbon atom.

16. The method according to claim 14 wherein the ester groups are rendered different from one another by containing substituted heteroatoms selected from N, O, and P.

17. The method according to claim 14, wherein at least one smaller ester group is selected and at least one larger ester group is selected, and the ester groups differ by at least one carbon atom.

18. The method according to claim 17, wherein a number ratio of the large ester group to the small ester group ranges from about 0.1 to about 0.9.

19. The method according to claim 17, wherein the smaller ester group ranges from 2 to 5 carbon atoms and the larger ester group ranges from 6 to 18 carbon atoms.

20. The method according to claim 14 further comprising selecting a mixture of a short chain and longer chain anhydrides by controlling the ratio of short chain to long chain anhydrides, wherein small anhydrides when reacted provide 2 to 6 carbon atoms in a first ester and large anhydrides when reacted provide 6 to 18 carbon atoms in a second ester.

21. The method according to claim 14, wherein sterically hindering ester groups are added.

22. The method according to claim 21, wherein the sterically hindering ester groups are isobutyrate, 2-ethylbutyrate, and/or 2-ethylhexanoate.

23. A method for making a modified triglyceride diester comprising a. providing an epoxidized triglyceride;

b. reacting the epoxidized triglyceride with an acid anhydride in the presence of a basic catalyst to produce a diester by heating essentially all components except the basic catalyst first and then adding the basic catalyst at an elevated temperature; and c. separating the diester from the catalyst and unreacted anhydride.

24. The method according to claim 23, wherein two or more different anhydrides are reacted.

25. The method according to claim 23, wherein the basic catalyst is a metal carbonate, bicarbonate, hydroxide, or carboxylate.

26. The method according to claim 23, wherein the basic catalyst is selected from the group consisting of $K_2CO_3$, $Na_2CO_3$, $KHCO_3$, and $NaHCO_3$.

27. The method according to claim 23, wherein a carboxylic acid is added as a secondary catalyst.

28. The method according to claim 23, wherein the basic catalyst is separated with water partitioning and excess anhydride is hydrolyzed to its corresponding carboxylic acid.

29. The method according to claim 23, wherein the excess anhydride is hydrolyzed by steam to the corresponding carboxylic acid and removed by deodorization.

30. A method for making a modified triglyceride diester comprising a. providing an epoxidized triglyceride;

b. reacting the epoxidized triglyceride with an acid anhydride in the presence of a basic catalyst and a carboxylic acid is added as a secondary catalyst to produce a diester; and c. separating the diester from the catalyst and unreacted anhydride.

31. The method according to claim 30, wherein two or more different anhydrides are reacted.

32. The method according to claim 30, wherein the basic catalyst is a metal carbonate, bicarbonate, hydroxide, or carboxylate.

33. The method according to claim 30, wherein the basic catalyst is selected from the group consisting of $K_2CO_3$, $Na_2CO_3$, $KHCO_3$, and $NaHCO_3$.

34. The method according to claim 30, wherein the reacting is performed by heating essentially all components except the basic catalyst first and then adding the basic catalyst at an elevated temperature.

35. The method according to claim 30, wherein the basic catalyst is separated with water partitioning and excess anhydride is hydrolyzed to its corresponding carboxylic acid.

36. The method according to claim 30, wherein the excess anhydride is hydrolyzed by steam to the corresponding carboxylic acid and removed by deodorization.

* * * * *

UNITED STATES PATENT AND TRADEMARK OFFICE

CERTIFICATE OF CORRECTION

PATENT NO. : 8,357,643 B2
APPLICATION NO. : 11/573494
DATED : January 22, 2013
INVENTOR(S) : Benecke et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1130 days.

Signed and Sealed this
First Day of September, 2015

Michelle K. Lee
*Director of the United States Patent and Trademark Office*